United States Patent
Abitabilo et al.

(10) Patent No.: US 11,202,897 B2
(45) Date of Patent: Dec. 21, 2021

(54) CLOSED SYSTEM CATHETER VENT CAP

(71) Applicant: Smiths Medical ASD, Inc., Plymouth, MN (US)

(72) Inventors: James Edward Abitabilo, Bristol, CT (US); Michael Blackwell, Winstead, CT (US); Jay T. Breindel, St. Louis Park, MN (US); Harsh D. Chheda, Cheshire, CT (US); Kathryn Felicito, Cheshire, CT (US); David J. Goral, Brookfield, CT (US); Christopher Roehl, New Hartford, CT (US)

(73) Assignee: Smiths Medical ADS, Inc., Plymouth, MN (US)

(*) Notice: Subject to any disclaimer, the term of this patent is extended or adjusted under 35 U.S.C. 154(b) by 256 days.

(21) Appl. No.: 16/315,044

(22) PCT Filed: Jul. 6, 2017

(86) PCT No.: PCT/US2017/040887
§ 371 (c)(1),
(2) Date: Jan. 3, 2019

(87) PCT Pub. No.: WO2018/009653
PCT Pub. Date: Jan. 11, 2018

(65) Prior Publication Data
US 2020/0009366 A1 Jan. 9, 2020

Related U.S. Application Data

(60) Provisional application No. 62/358,982, filed on Jul. 6, 2016.

(51) Int. Cl.
*A61M 39/20* (2006.01)
*A61M 25/06* (2006.01)
*A61M 39/10* (2006.01)

(52) U.S. Cl.
CPC ........ *A61M 39/20* (2013.01); *A61M 25/0606* (2013.01); *A61M 39/10* (2013.01); *A61M 2039/205* (2013.01)

(58) Field of Classification Search
CPC .. A61M 39/20; A61M 25/0606; A61M 39/10; A61M 2039/205; A61M 25/06;
(Continued)

(56) References Cited

U.S. PATENT DOCUMENTS 5,000,740 A   3/1991  Ducharme et al.
5,441,487 A * 8/1995  Vedder ............... A61M 39/045
                                                604/167.03
(Continued)

FOREIGN PATENT DOCUMENTS

CN        1627971 A    6/2005
CN      201806995 U    4/2011
(Continued)

OTHER PUBLICATIONS

International Search Report for corresponding International Application No. PCT/US2017/040887 dated Oct. 16, 2017; 4 pages.
(Continued)

*Primary Examiner* — Theodore J Stigell
*Assistant Examiner* — Rachel T. Smith
(74) *Attorney, Agent, or Firm* — Patterson Thuente Pedersen, P.A.

(57) ABSTRACT

A self activating vent cap configured to be operably coupled to a needleless connector and automatically shifted relative to the needleless connector from the first, storage position to a second, activated position upon rotation of the vent cap relative to the needleless connector. The self activating vent cap including a threaded portion, an activation portion and a biasing mechanism, wherein shifting of the activation portion to the second, activated position is selectively pre- (Continued)

cluded by the interference of at least one ridge of the threaded portion with a ledge of the activation portion.

4 Claims, 26 Drawing Sheets

(58) Field of Classification Search
CPC ...... A61M 39/06; A61M 39/24; A61M 39/26; A61M 25/0097; A61M 2039/027; A61M 2039/062; A61M 2039/0633; A61M 2039/0673; A61M 2039/226; A61M 2039/1027–1038; A61M 39/00; A61M 39/22
See application file for complete search history.

(56) References Cited

U.S. PATENT DOCUMENTS

| | | |
|---|---|---|
| 6,872,193 B2 | 3/2005 | Shaw et al. |
| 7,291,130 B2 | 11/2007 | McGurk |
| 7,713,248 B2 | 5/2010 | Lopez |
| 7,736,342 B2 | 6/2010 | Abriles et al. |
| 8,257,322 B2 | 9/2012 | Koehler et al. |
| 9,114,231 B2 | 8/2015 | Woehr et al. |
| 2003/0083621 A1 | 5/2003 | Shaw et al. |
| 2013/0338588 A1 | 12/2013 | Grimm et al. |
| 2014/0276434 A1 | 9/2014 | Woehr et al. |
| 2014/0276458 A1 | 9/2014 | Mansour et al. |
| 2014/0276462 A1 | 9/2014 | Vincent et al. |
| 2016/0220791 A1 | 8/2016 | Akcay et al. |

FOREIGN PATENT DOCUMENTS

| | | |
|---|---|---|
| CN | 102573953 A | 7/2012 |
| CN | 102883764 A | 1/2013 |
| CN | 104043180 A | 9/2014 |
| CN | 105050654 A | 11/2015 |
| CN | 105228689 A | 1/2016 |
| EP | 0451040 A1 | 10/1991 |
| EP | 2968907 A1 | 1/2016 |
| WO | WO 2014/150530 A1 | 9/2014 |

OTHER PUBLICATIONS

Written Opinion of the International Searching Authority for corresponding International Application No. PCT/US2017/040887 dated Oct. 16, 2017; 7 pages.
Communication dated Jul. 7, 2020 for EP Application No. 17824880.3, 9 pages.

\* cited by examiner

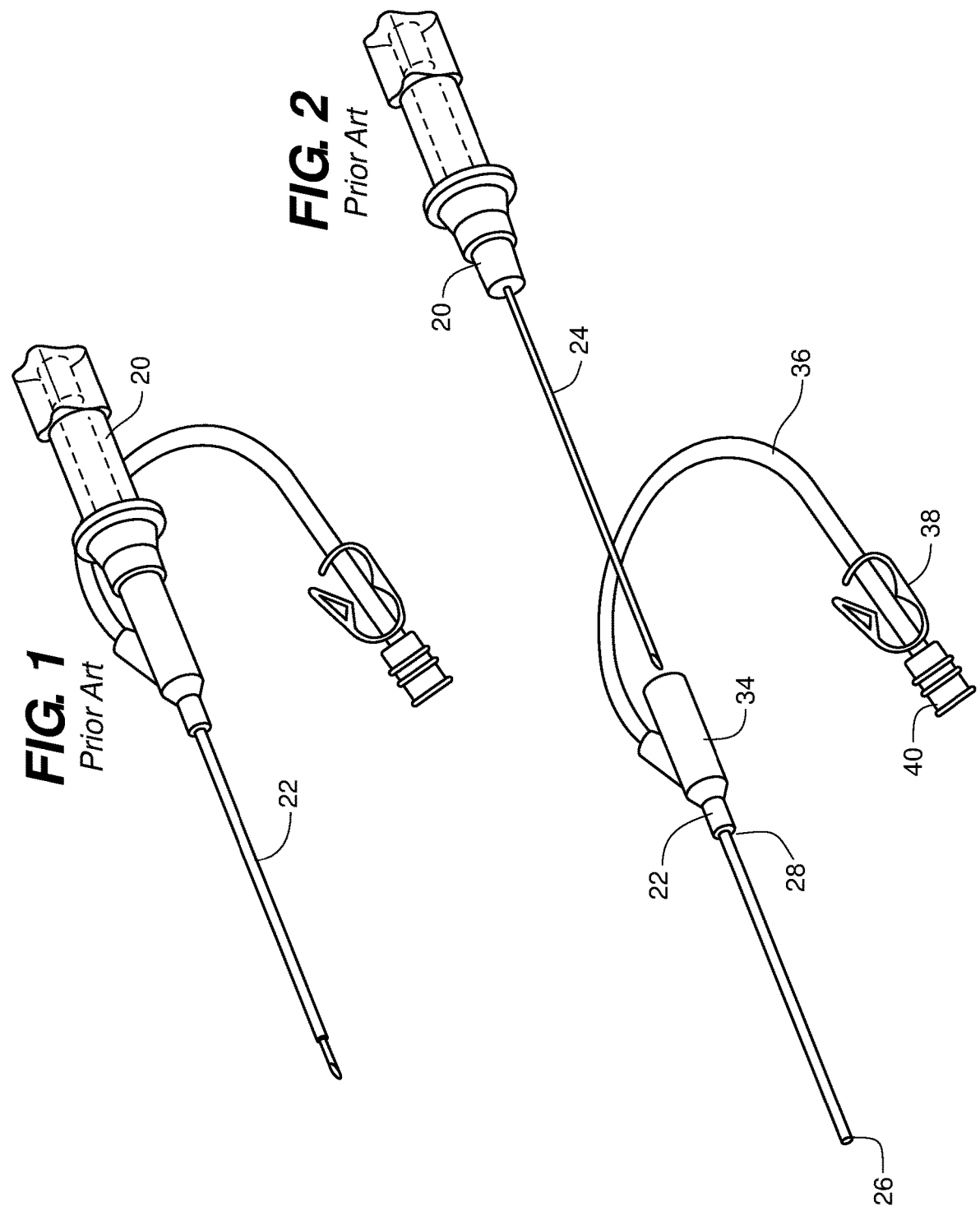

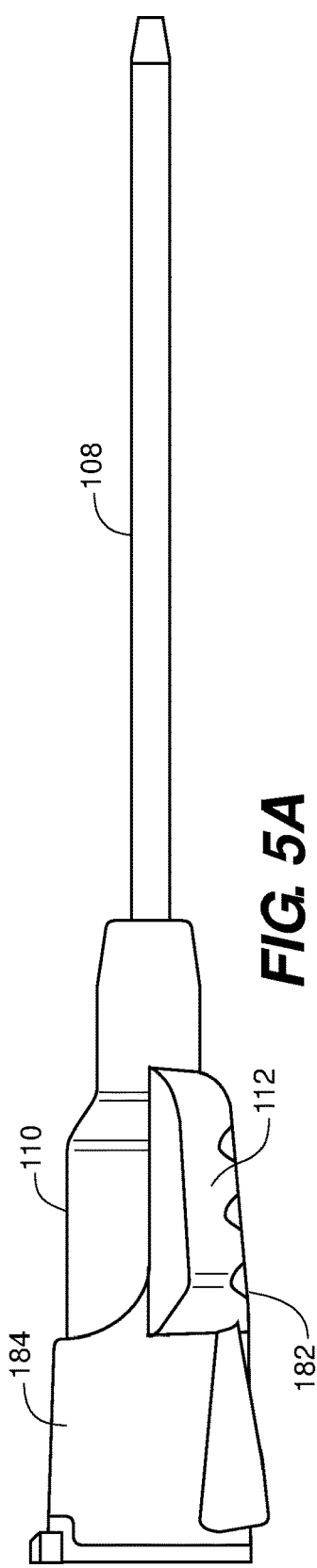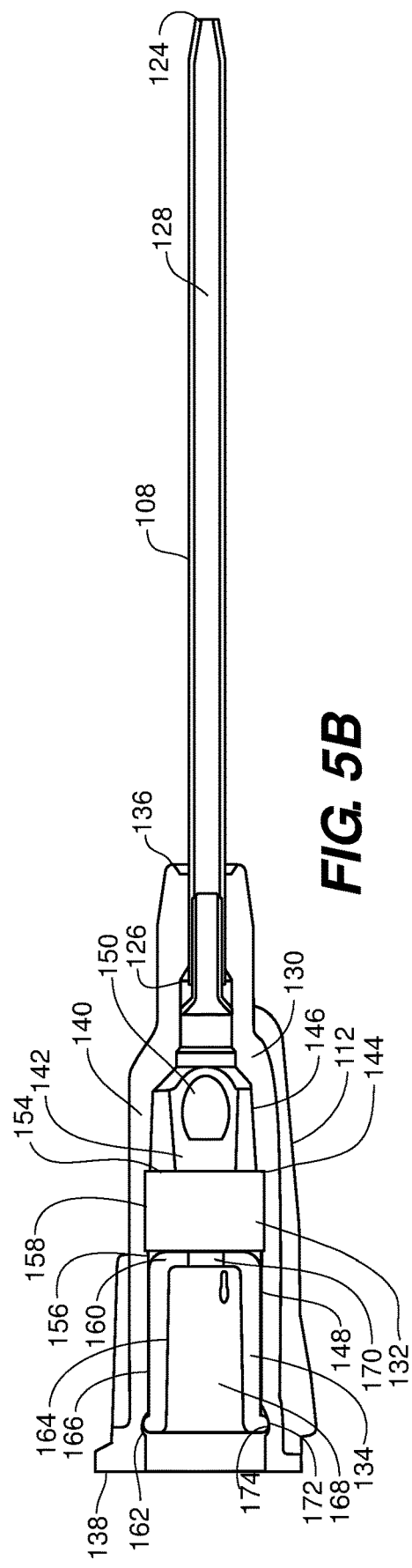

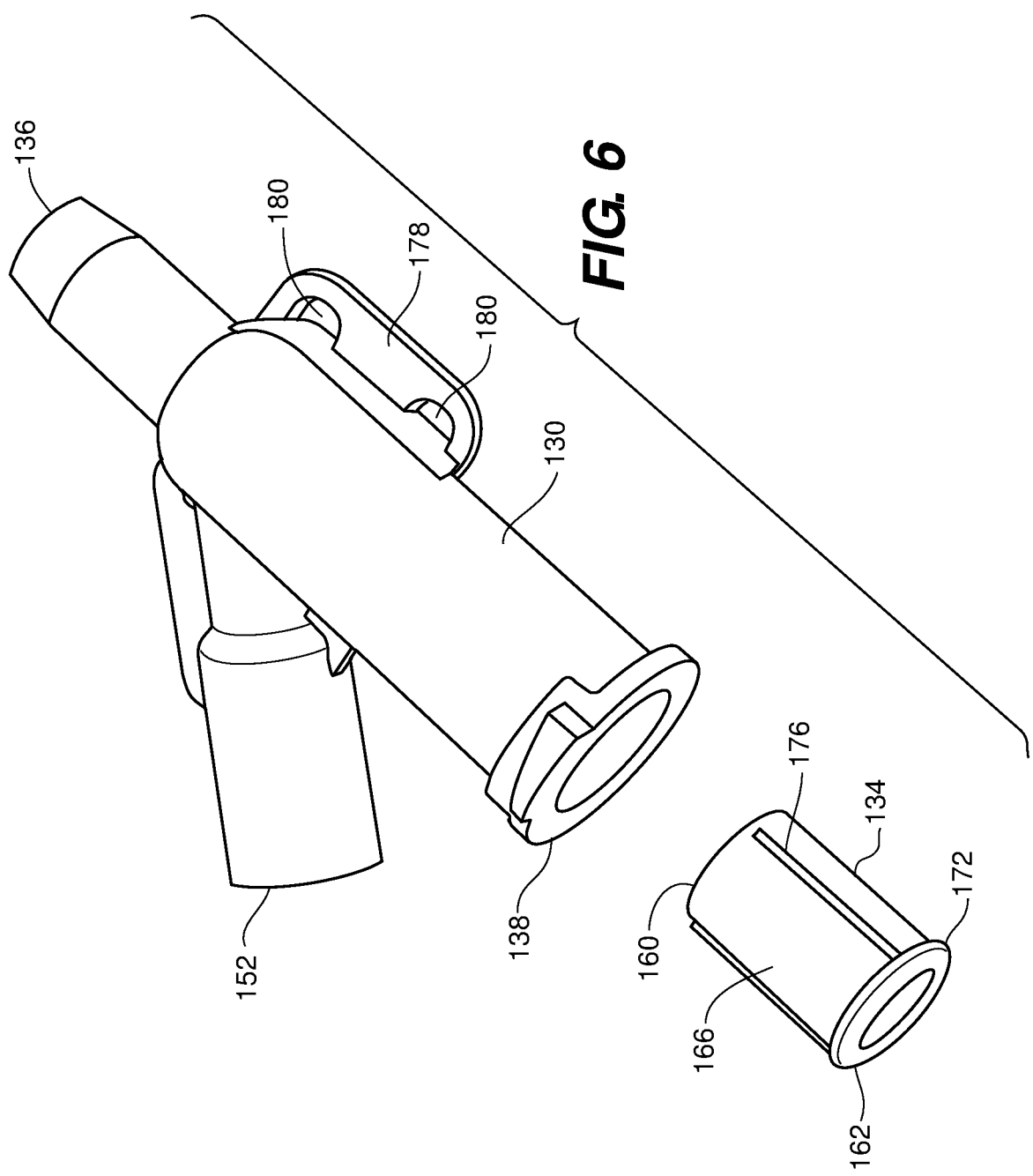

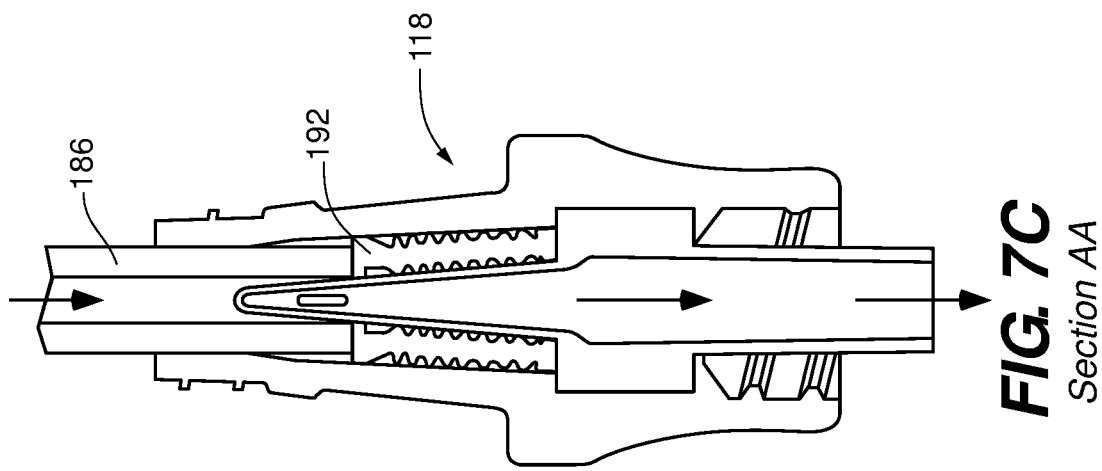
FIG. 7C Section AA
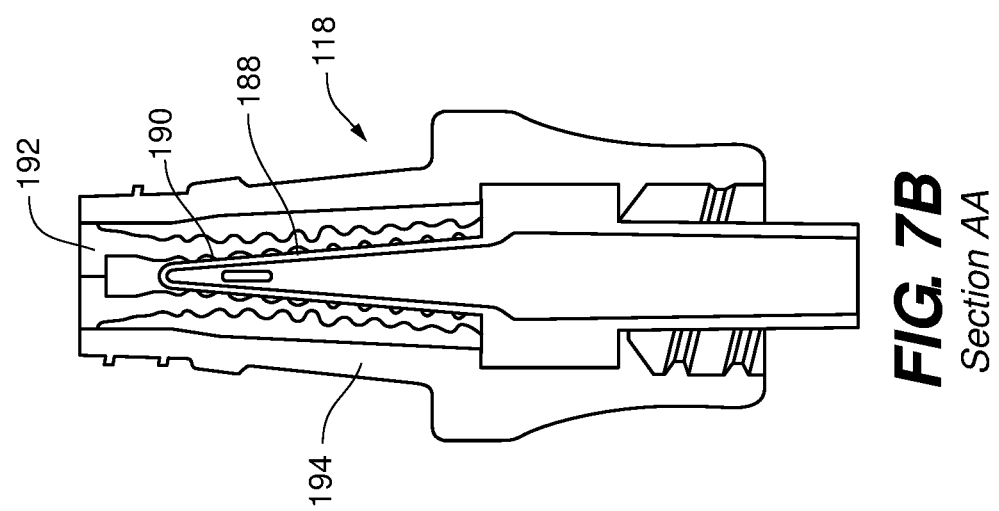
FIG. 7B Section AA
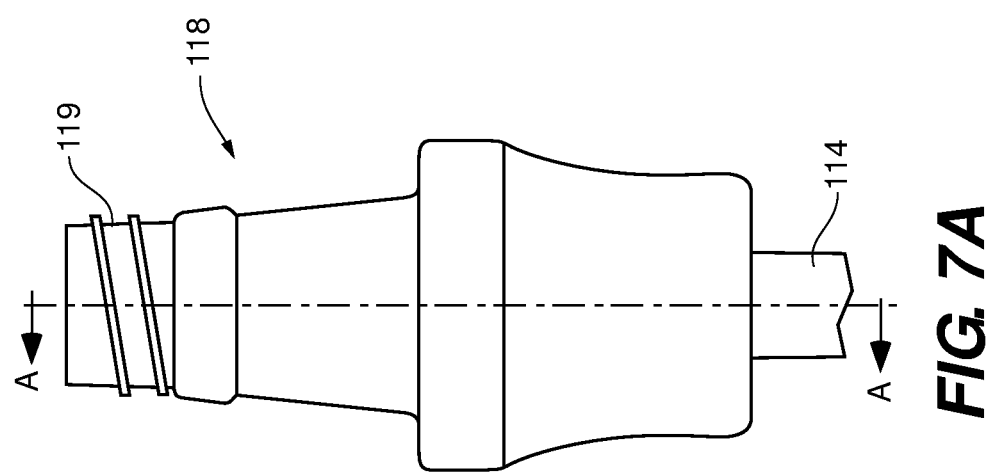
FIG. 7A

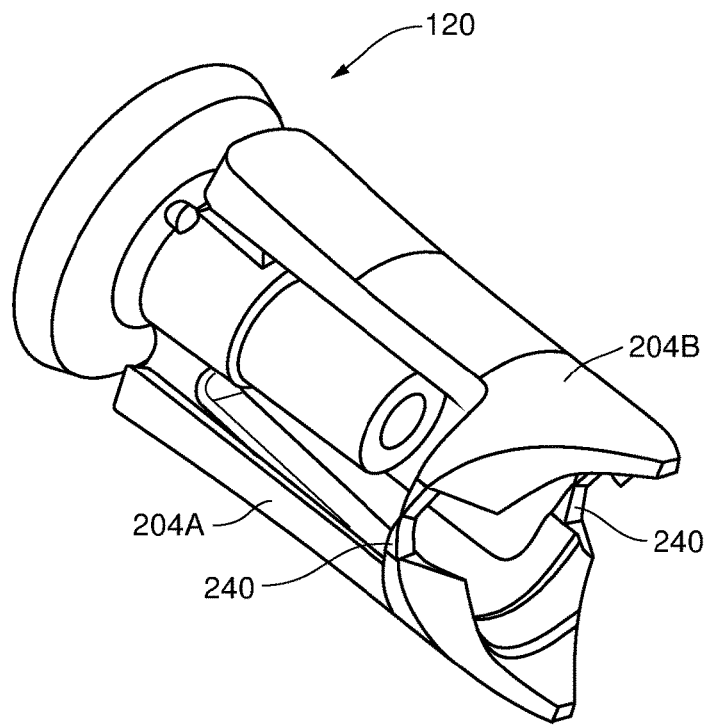
FIG. 20
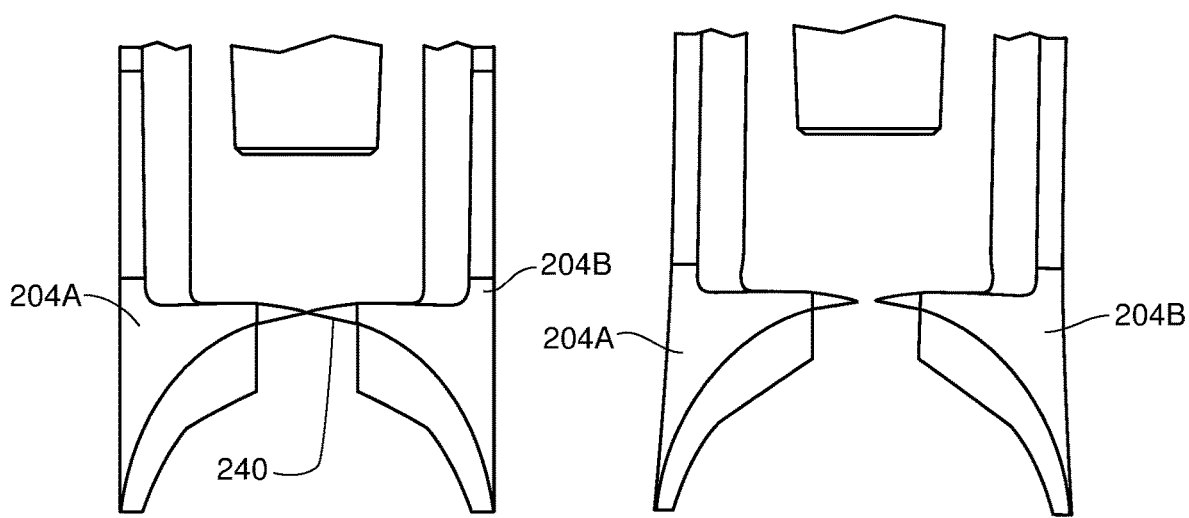
FIG. 21A  FIG. 21B

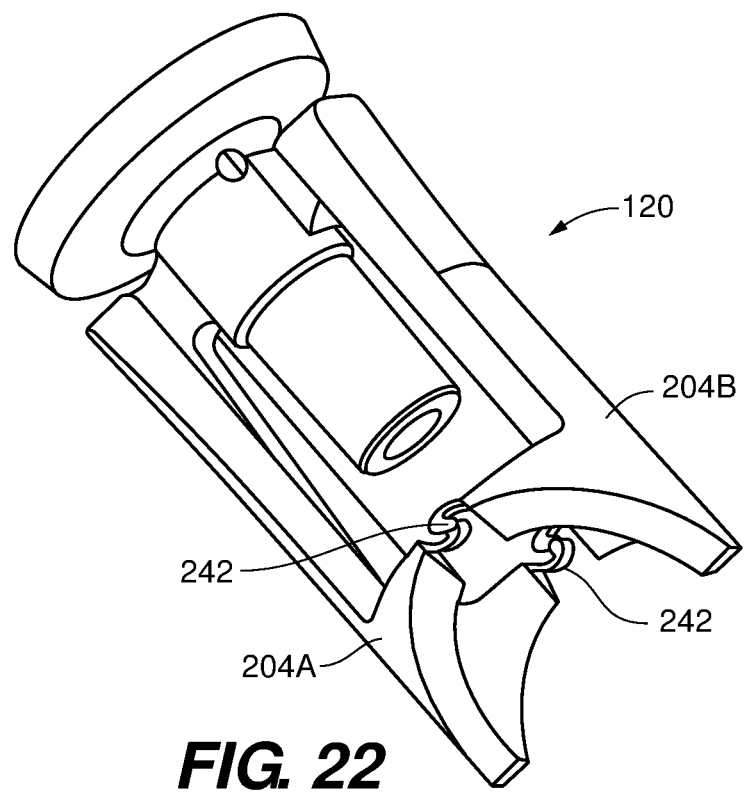
FIG. 22
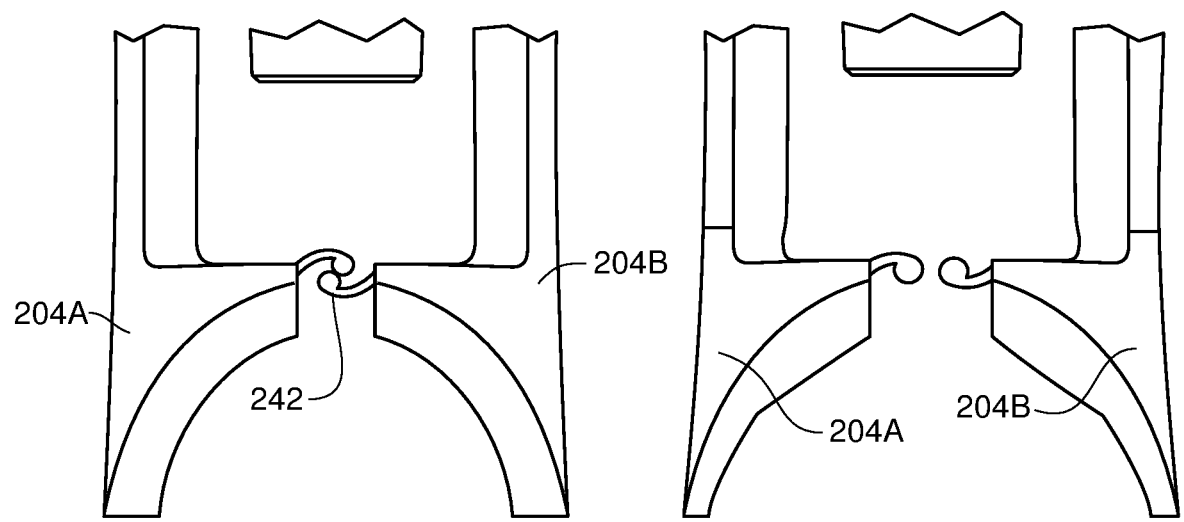
FIG. 23A  FIG. 23B

CLOSED SYSTEM CATHETER VENT CAP

CROSS REFERENCE TO RELATED APPLICATIONS

The present application is a National Phase Entry of PCT Application No. PCT/US2017/040887, filed Jul. 6, 2017, which claims the benefit of U.S. Provisional Application No. 62/358,982 filed Jul. 6, 2016, which are hereby incorporated herein in its entirety by reference.

RELATED APPLICATION

The present application claims the benefit of U.S. Provisional Application No. 62/358,982 filed Jul. 6, 2016, which is hereby incorporated herein in its entirety by reference.

TECHNICAL FIELD

The present disclosure relates generally to intravenous catheters, and more particularly to a closed system intravenous catheter assembly that enables the venting of gas within an intravenous catheter assembly prior to connection to an IV fluid supply.

BACKGROUND

Intravenous (IV) therapy is a versatile technique used for the administration of medical fluids to and withdrawal of bodily fluids from patients. IV therapy has been used for various purposes such as the maintenance of fluid and electrolyte balance, the transfusion of blood, the administration of nutritional supplements, chemotherapy, and the administration of drugs and medications. These fluids, collectively referred to herein as medicaments, may be administered intravenously by injection through a hypodermic needle, or intermittent or continuously by infusion using a needle or catheter. A common intravenous access device utilized by clinicians is the peripheral IV catheter.

A peripheral IV catheter is made of soft, flexible plastic or silicone, generally between fourteen and twenty-four gauge in size. In the conventional venipuncture procedure, a catheter is inserted into a vein in the patient's hand, foot, or the inner aspect of the arm or any vein in the body that will accept an IV catheter. In order to place the IV catheter into the patient's vein, a sharp introducer needle is used to puncture the skin, tissue, and vein wall to provide a path for placement of the catheter into the vein.

Referring to FIGS. 1 and 2, a conventional IV needle assembly 20 configured for insertion of an "over the needle" catheter 22 is depicted. Catheter 22 generally has a distal end 26 for insertion into a biological site, a proximal end 28 and a flexible wall defining a lumen extending therebetween. Frequently, the proximal end 28 of the catheter 22 is operably coupled to a catheter hub 34. Catheter 22 can be operably coupleable to the needle assembly 20, in part by positioning the catheter 22 coaxially over a needle 24 of the needle assembly 20. The catheter 22 thus rides with the needle 24 through the skin, tissue and vein wall and into the patient's vein. Once the catheter 22 has been entered into the patient's vein, the catheter 22 can be advanced further into the vein as desired and the needle 24 can be withdrawn from the catheter 22. The catheter can then be secured into place on the patient and connected to an IV fluid supply line. In some instances, catheter 22 can include an extension tube 36 having a clamp 38 and a Luer lock connector 40 for connection to an IV fluid supply.

SUMMARY OF THE DISCLOSURE

Embodiments of the present disclosure provide a closed system intravenous catheter assembly, which enables the venting of the gas trapped within an intravenous catheter assembly without exposing a clinician to blood that enters the intravenous catheter assembly during catheter insertion. Additionally, exposure of the interior of the intravenous catheter assembly to the ambient environment is minimized, thereby minimizing the risk of unwanted contaminants becoming introduced into the interior of the intravenous catheter assembly. Moreover, embodiments of the present disclosure can provide a positive indication, such as an audible noise, tactile, or visual indication, to a user that the intravenous catheter assembly has properly been shifted to the gas venting position, or that gas trapped within the intravenous catheter assembly has been properly vented.

One embodiment of the present disclosure provides a self activating vent cap configured to be operably coupled to a needleless connector and automatically shifted relative to the needleless connector from a first, storage position to a second, activated position upon rotation of the vent cap relative to the needleless connector. The vent cap can include a threaded portion, an activation portion, and a biasing mechanism. The threaded portion can be configured to be selectively threadably coupled to the needleless connector, such that the threaded portion is coupled to the needleless connector during use, and is uncoupled from the needleless connector after use. The activation portion can at least partially surround the threaded portion and can be shiftable relative to the threaded portion between the first, storage position in which the needleless connector remains sealed, and the second, activated position, in which a wall defining a vent path is at least partially inserted into the needleless connector, thereby enabling gas within the needleless connector to vent therefrom. The biasing mechanism can be positioned between the threaded portion and the activation portion and can be configured to bias the activation portion to the second, activated position. Shifting of the activation portion to the second, activated position can be selectively precluded by the interference of at least one ridge of the threaded portion with a ledge of the activation portion. The activation portion can be configured to rotate relative to the threaded portion to reduce interference between the at least one ridge and the ledge, thereby enabling the activation portion to shift to the second, activated position.

Another embodiment of the present disclosure provides a self activating vent cap configured to be operably coupled to a needleless connector and automatically shifted relative to the needleless connector from a first, storage position to a second, activated position upon removal of a blocking member. The vent cap can include a threaded portion, an activation portion, and a biasing mechanism. The threaded portion can be configured to be selectively threadably coupled to the needleless connector, such that the threaded portion is coupled to the needleless connector during use, and is uncoupled from the needleless connector after use. The activation portion can at least partially surround the threaded portion and can be shiftable relative to the threaded portion between the first, storage position, in which the needleless connector remains sealed, and the second, activated position, in which a wall defining a vent path is at least partially inserted into the needleless connector, thereby enabling gas within the needleless connector to vent therefrom. The biasing mechanism can be positioned between the threaded portion and the activation portion and can be configured to bias the activation portion to the second, activated position. Shifting of the activation portion to the second, activated position can be inhibited by a blocking member inserted into an aperture defined within the activation portion. Upon removal of the blocking member, the biasing mechanism can bias the activation portion to the second, activated position.

Another embodiment of the present disclosure provides a vent cap configured to be coupled to a needleless connector and shiftable relative to the needleless connector between a storage position and an actively depressed, venting position. The vent cap can include a threaded portion and an activation portion. The threaded portion can be configured to be selectively threadably coupled to the needleless connector, such that the threaded portion is coupled to the needleless connector during use, and is uncoupled from the needleless connector after use. The activation portion can at least partially surround the threaded portion and can be shiftable relative to the threaded portion between the storage position, in which the needleless connector remains sealed, and the actively depressed, venting position in which a wall defining a vent path is at least partially inserted into the needleless connector, thereby enabling gas within the needleless connector to vent therefrom. The vent cap can be configured such that actively depressing the activation portion distally to the actively depressed, venting position enables the threaded portion to be threadably uncoupled from the needleless connector.

Another embodiment of the present disclosure provides a vent cap configured to be operably coupled to a needleless connector and shiftable relative to the needleless connector between a storage position and an actively depressed, venting position. The vent cap can include a nose configured to be inserted at least partially into the needleless connector when the vent cap is shifted to the actively depressed, venting position, wherein the nose includes a reverse taper such that a force to shift the vent cap from the storage position to the actively depressed, venting position decreases as the vent cap approaches the actively depressed, venting position, thereby causing a contact between an abutting surface of the nose and a portion of the needleless connector resulting in an audible clicking sound to positively indicate that the vent cap has been shifted to the actively depressed, venting position.

In one embodiment, the vent cap further includes one or more engagement arms configured to grip a portion of the needleless connector. In one embodiment, the one or more engagement arms are constructed of a resilient material configured to bias the vent cap to the storage position when coupled to the needleless connector. In one embodiment, the nose includes one or more ribs positioned along an outer surface of the nose. In one embodiment, the ribs are configured to provide frictional interference with an internal surface of the needleless connector. In one embodiment, the nose includes a vent path wall defining a vent path. In one embodiment, an air permeable membrane is positioned within a portion of the vent path. In one embodiment, in the actively depressed, venting position, the vent path is configured to fill with a bodily fluid, so as to provide a visual confirmation of proper venting. In one embodiment, a portion of the vent path wall includes an eyelet configured to provide a secondary path for venting air between the vent path and an exterior of the vent path wall.

Another embodiment of the present disclosure provides a medical connector operably coupled to an intravenous catheter configured to be selectively coupled to an IV fluid supply line. The medical connector can include a conical internal conduit, a flexible compression seal and a housing. The conical internal conduit can include one or more fluid path windows. The flexible compression seal can be biased to a closed position to seal the one or more fluid path windows when an IV fluid supply line is not connected, and can be shiftable to a compressed position to open the one or more fluid path windows when an IV fluid supply line is connected. The flexible compression seal can include a coil spring configured to bias the compression seal to the closed position. The housing can substantially surround the internal conduit and a flexible compression seal.

Another embodiment of the present disclosure provides a medical connector operably coupled to an intravenous catheter and configured to be selectively coupled to an IV fluid supply line. The medical connector can include a conical internal conduit, a flexible compression seal, a housing, and a seal ring. The conical internal conduit can define one or more fluid path windows. The flexible compression seal can be biased to a closed position to seal the one or more fluid path windows when an IV fluid supply line is not connected, and can be shiftable to a compressed position to open the one or more fluid path windows when an IV fluid supply line is connected. The housing can substantially surround an internal conduit and a flexible compression seal, wherein the housing defines a vent aperture comprising an air permeable barrier configured to enable gas within the medical connector to vent to the atmosphere. The sealing ring can be configured to shift from a first, initial venting position to a second, vent sealing position in which the air permeable membrane is at least partially covered by the sealing ring, wherein the shifting of the sealing ring is affected by the connection of an IV fluid supply connector to the housing.

Another embodiment of the present disclosure provides a medical connector operably coupled to an intravenous catheter and configured to be selectively coupled to an IV fluid supply line. The medical connector can include a housing, a spool valve, a seal, and a coil spring. The housing can define a vent aperture comprising an air permeable barrier. The spool valve can reside within the housing and can be shiftable between an internal, venting position, an IV fluid supply line open position, and a closed position. The seal can be operably coupled to the spool valve and shiftable relative to the spool valve between a distal position and a proximal position. The coil spring can be configured to bias the spool valve to the closed position. In the initial, venting position, the seal can be shifted to the distal position relative to the spool valve such that the vent aperture is opened, thereby enabling gas within the medical connector to vent through the air permeable barrier. When the IV fluid supply line is coupled to the medical connector, the spool valve can shift to an IV fluid supply line open position and the seal can shift to the proximal position relative to the spool valve, thereby opening a fluid connection to the IV fluid supply line and sealing the vent aperture. When the IV fluid supply connector is uncoupled from the medical connector, the spool valve can shift to the closed position and the seal can shift to the distal position relative to the spool valve, thereby closing the fluid connection to the IV fluid supply line to maintain the seal of the vent aperture.

Another embodiment of the present disclosure provides a medical connector operably coupled to an intravenous catheter and configured to be selectively coupled to an IV fluid supply line. The medical connector can include a needleless connector and a vent cap. The needleless connector can be shiftable between an initial, sealed position, in which a seal inhibits the fluid from passing through the needleless connector, and a flow position in which the seal is opened to enable fluid to flow from the IV fluid supply line to the intravenous catheter. The vent cap can be operably coupled to the needleless connector, and shiftable relative to the needleless connector between a storage position in an actively depressed, venting position. The vent cap can include a nose, a push plate, and one or more needleless connector engagement arms. The nose can be configured to be inserted at least partially into the needleless connector when the vent cap is shifted to the actively depressed, venting position. The push plate can define a vent aperture comprising an air permeable barrier. The one or more needleless connector engagement arms can be configured to grip a portion of the needleless connector. Structure defined by at least one of the nose and the one or more needleless connector engagement arms can be configured to create an audible clicking sound to positively indicate that the vent cap is shifted to the actively depressed, venting position.

Another embodiment of the present disclosure provides a vent cap configured to be operably coupled to a needleless connector and shiftable relative to the needleless connector between a storage position and an actively depressed, venting position. The vent cap can include a nose, a push plate, and one or more needleless connector engagement arms. The nose can be configured to be inserted at least partially into the needleless connector when the vent cap is shifted to the actively depressed, venting position. The push plate can define a vent aperture comprising an air permeable membrane. The one or more needleless connector engagement arms can be configured to grip a portion of the needleless connector. Structure defined by at least one of the nose and the one or more needleless connector engagement arms can be configured to create an audible clicking sound to positively indicate that the vent cap has been shifted to the actively depressed, venting position.

Another embodiment of the present disclosure provides a vent cap configured to be operably coupled to a needleless connector and shiftable relative to the needleless connector between a storage position and an actively depressed, venting position. The vent cap can include a nose, a push plate and one or more needleless connector engagement arms. The nose can be configured to be inserted at least partially into the needleless connector when the vent cap is shifted to the actively depressed, venting position. The push plate can define a vent aperture comprising an air permeable barrier. The one or more needleless connector engagement arms can be configured to grip a portion of the needleless connector, wherein the one or more needleless connector engagement arms each include a breakable joint configured to be broken when the vent cap is shifted to the actively depressed, venting position, thereby creating an audible clicking sound to positively indicate that the vent cap has been shifted to the actively depressed, venting position.

Another embodiment of the present disclosure provides a vent cap configured to be operably coupled to a needleless connector and shiftable relative to the needleless connector between a storage position and an actively depressed, venting position. The vent cap can include a nose, a push plate and one or more needleless connector engagement arms. The nose can be configured to be inserted at least partially into the needleless connector when the vent cap is shifted to the actively depressed, venting position. The push plate can define a vent aperture comprising an air permeable barrier. The one or more needleless connector engagement arms can be configured to grip a portion of the needleless connector, wherein the one or more needleless connector engagement arms each include opposed hooks configured to be uncoupled from one another when the vent cap is shifted to the actively depressed, venting position, thereby creating an audible clicking sound to positively indicate that the vent cap has been shifted to the actively depressed, venting position.

Another embodiment of the present disclosure provides a vent cap configured to be operably coupled to the needleless connector and shiftable relative to the needleless connector between a storage position and an actively depressed, venting position. The vent cap can include a nose, a push plate, and one or more needleless connector engagement arms. The nose can be configured to be inserted at least partially into the needleless connector when the vent cap is shifted to the actively depressed, venting position, wherein the nose includes a color-coded visual indicator configured to indicate the position of the vent cap relative to the needleless connector. The push plate can define a vent aperture comprising an air permeable barrier. The one or more needleless connector engagement arms can be configured to grip a portion of the needleless connector.

Another embodiment of the present disclosure provides a vent cap configured to be coupled to the needleless connector of an intravenous catheter assembly and shiftable relative to the needleless connector between a storage position and an actively depressed, venting position. The vent cap can include a nose, a threaded portion and a tether. The nose can be configured to be inserted at least partially into the needleless connector when the vent cap is shifted to the actively depressed, venting position. The threaded portion can be configured to be threadably coupled to the needleless connector. The tether can operably couple the vent cap to the intravenous catheter assembly.

Another embodiment of the present disclosure provides a vent cap configured to be coupled to a needleless connector and shiftable relative to the needleless connector between a storage position and an actively depressed, venting position. The vent cap can include a nose and a threaded portion. The nose can be configured to be at least partially inserted into the needleless connector when the vent cap is shifted to the actively depressed, venting position. The threaded portion can be configured to be threadably coupled to the needleless connector. Rotation of the threaded portion in a first direction relative to the needleless connector can cause the threaded portion to shift to the actively depressed venting position. Further rotation of the threaded portion in the first direction can cause the threaded portion to omit an audible clicking sound to positively indicate that the vent cap has been properly shifted to the actively depressed, venting position.

Another embodiment of the present disclosure provides a reversible vent cap configured to be coupled to a needleless connector in a storage position, such that the vent cap can be selectively removed from the needleless connector and manipulated into a venting position. The vent cap can include a connector end and an activation end. The connector end can be configured to be operably coupled to the needleless connector, and can include a cup portion having an internal wall defining an internal thread configured to be threadably coupled to a Luer lock of the needleless connector. The activation end can be configured to be inserted at least partially into the needleless connector when the vent cap is manipulated into the venting position.

Another embodiment of the present disclosure provides a vent cap configured to be operably coupled to a needleless connector, so as to break a seal on a compression seal within a needleless connector. The vent cap can include a vent cap body having a connection portion, a venting portion and a mandrel. The connection portion can define a cup-shaped receptacle having an interior surface configured to operably couple to the needleless connector. The venting portion can define a vent path between the interior surface of the connection portion and the atmosphere. The mandrel can be at least partially housed within the vent path and can be configured to be inserted through a portion of the compression seal, thereby enabling gas trapped within the needleless connector to escape into the atmosphere.

Another embodiment of the present disclosure provides a vent cap configured to be operably coupled to a needleless connector, so as to break a seal on a compression seal within the needleless connector. The vent cap can include a vent cap body having a connection portion, a venting portion and a cannula. The connection portion can define a cup shaped receptacle having an interior surface configured to operably couple to the needleless connector. The venting portion can define a vent path opening at one end to the atmosphere. The cannula can define a fluid path between the interior surface of the connection portion and the vent path, thereby enabling gas trapped within the needleless connector to escape into the atmosphere.

The summary above is not intended to describe each illustrated embodiment or every implementation of the present disclosure. The figures and the detailed description that follow more particularly exemplify these embodiments.

BRIEF DESCRIPTION OF THE DRAWINGS

The disclosure can be more completely understood in consideration of the following detailed description of various embodiments of the disclosure, in connection with the accompanying drawings, in which:

FIG. 1 is a perspective view depicting a conventional IV needle assembly with a catheter positioned over a needle.

FIG. 2 is a perspective view depicting the conventional IV needle assembly of FIG. 1 with the catheter removed from the needle.

FIG. 5A is a profile view depicting a catheter tube, catheter hub and wings in accordance with an embodiment of the disclosure.

FIG. 5B is a cross sectional view of the catheter tube, catheter hub and wings of FIG. 5A.

FIG. 6 is an exploded perspective view of a catheter hub body and septum retainer in accordance with an embodiment of the disclosure.

FIG. 7A is an elevational, fragmentary view depicting a needleless connector in accordance with an embodiment of the disclosure, wherein the needleless connector is coupled to a connector tube.

FIG. 7B is a cross sectional view depicting the needleless connector of FIG. 7A in a closed configuration.

FIG. 7C is a cross sectional view depicting the needleless connector of FIG. 7A in an open configuration, in conjunction with an IV fluid supply.

FIG. 20 is a perspective view of a vent cap having a breakable joint in accordance with an embodiment of the disclosure.

FIG. 21A is a profile view depicting a portion of the vent cap of FIG. 20, wherein the breakable joint is unbroken.

FIG. 21B is a profile view depicting a portion of the vent cap of FIG. 20, wherein the breakable joint is broken.

FIG. 22 is a perspective view of a vent cap having opposing hooks in accordance with an embodiment of the disclosure.

FIG. 23A is a profile view depicting a portion of the vent cap of FIG. 22, wherein the opposing hooks are coupled to one another.

FIG. 23B is a profile view depicting a portion of the vent cap of FIG. 22, wherein the opposing hooks are uncoupled from one another.

Figure 3:
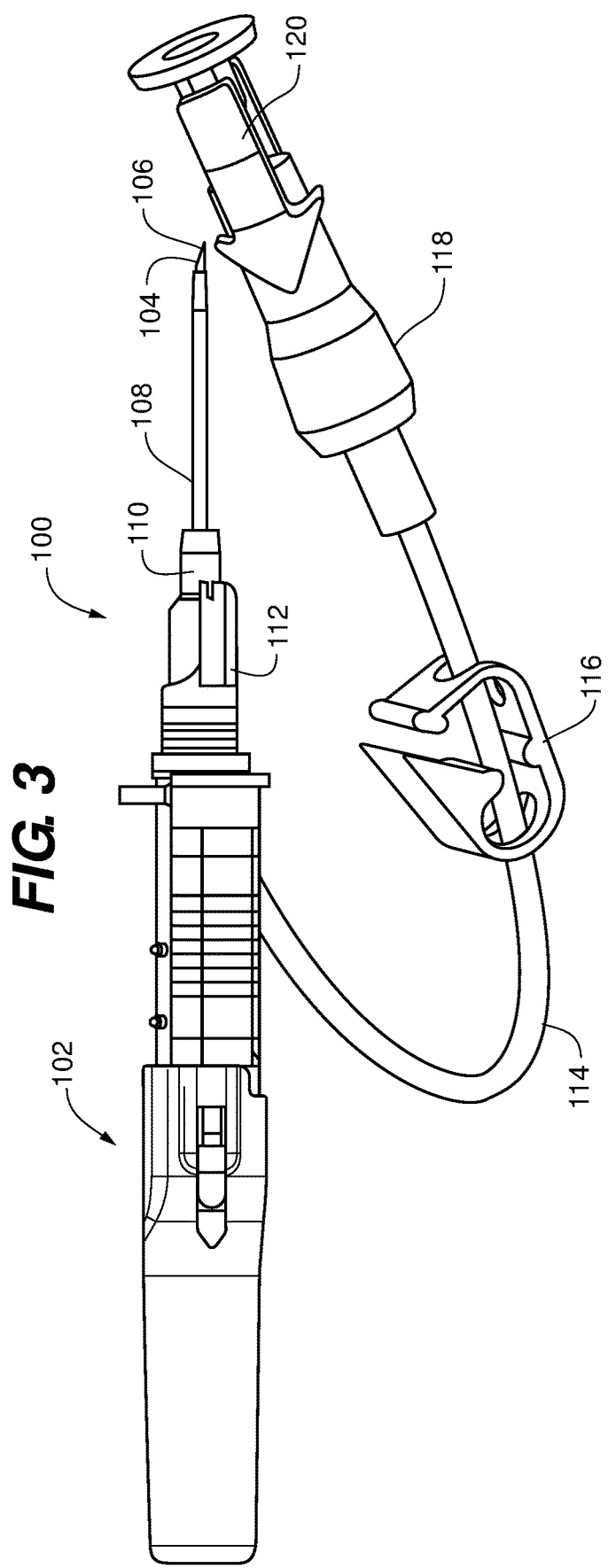
FIG. 3 is a profile view depicting an intravenous catheter assembly operably coupled to a catheter insertion device in accordance with an embodiment of the disclosure.

While embodiments of the disclosure are amenable to various modifications and alternative forms, specifics thereof are shown by way of example in the drawings and will be described in detail. It should be understood, however, that the intention is not to limit the disclosure to the particular embodiments described. On the contrary, the intention is to cover all modifications, equivalents, and alternatives falling within the spirit and scope of the disclosure as defined by the appended claims.

DETAILED DESCRIPTION

Referring to FIGS. 1 and 2, a conventional IV catheter assembly 20 is depicted. Details of the conventional IV catheter assembly 20 are described in the Background section above.

Figure 4B:
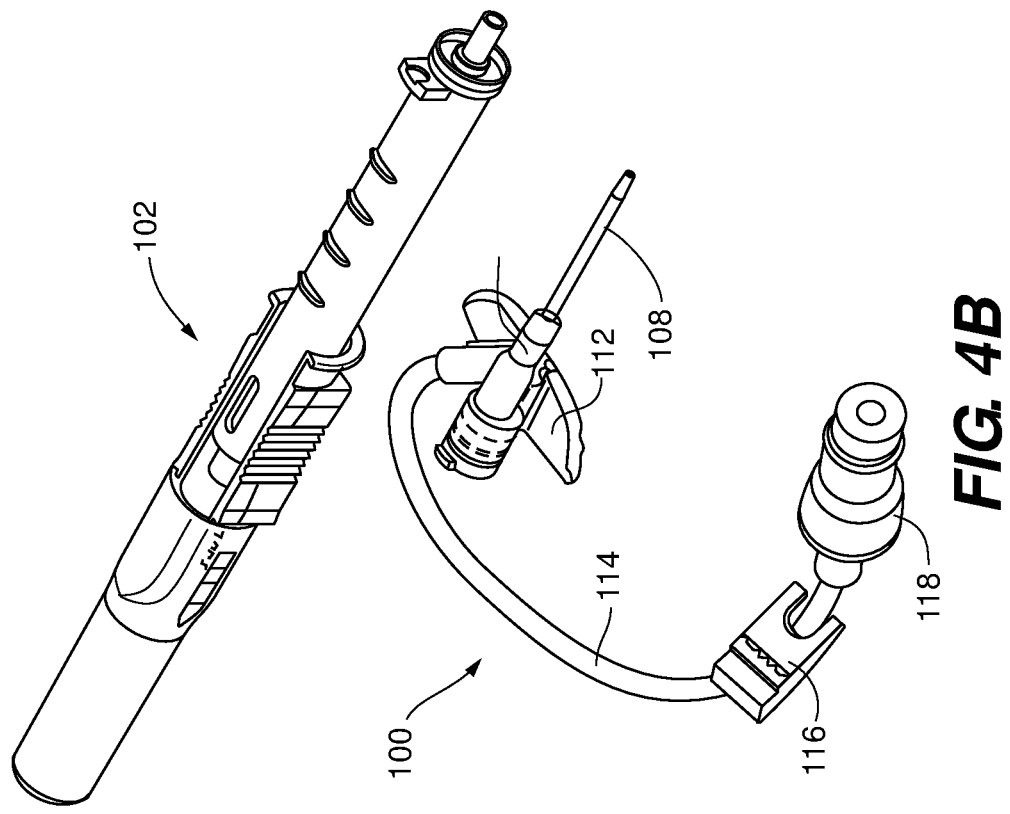
FIG. 4B is a perspective view of the intravenous catheter assembly and catheter insertion device of FIG. 4A, wherein the intravenous catheter assembly is decoupled from the catheter insertion device, and the catheter insertion device is in the needle retracted, safe position.
Figure 4A:
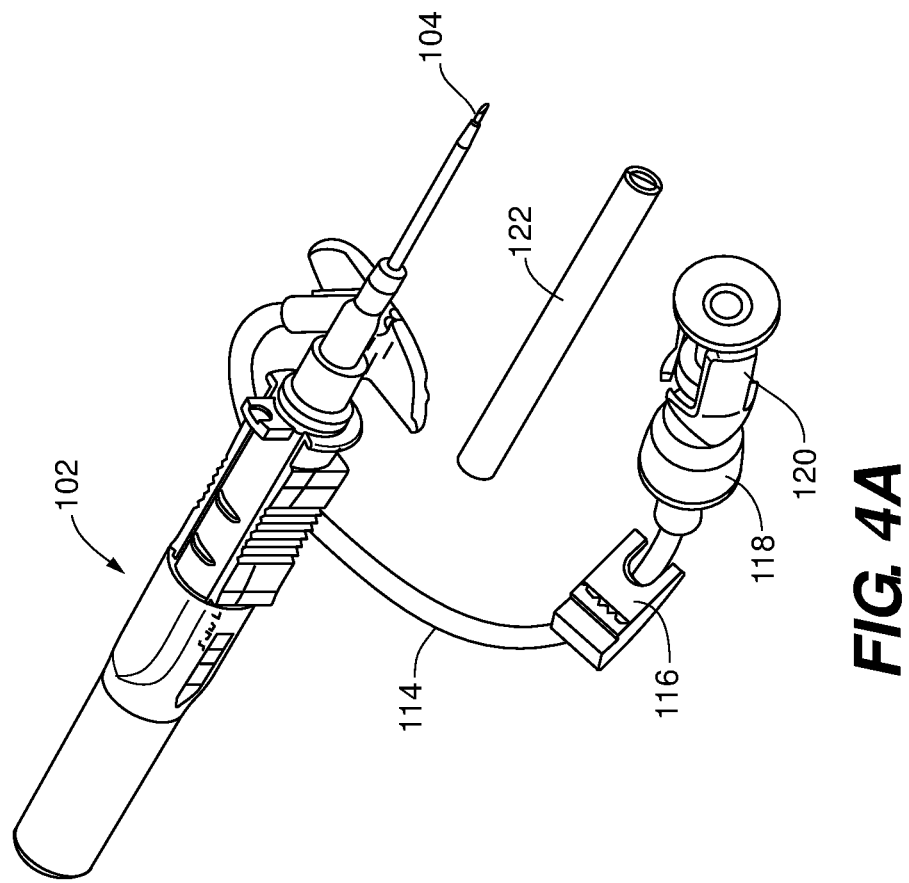
FIG. 4A is a perspective view depicting an intravenous catheter assembly operably coupled to a catheter insertion device in accordance with an embodiment of the disclosure, wherein the catheter insertion device is in the ready for use position.

Referring to FIGS. 3 and 4A-B, an intravenous catheter assembly 100 is depicted in accordance with an embodiment of the disclosure. As depicted, the intravenous catheter assembly can be selectively coupleable to a catheter insertion device 102.

I. Catheter Insertion Device

Catheter insertion device 102 can generally provide a needle 104, over which a portion of the intravenous catheter assembly 100 coaxially rides. In some embodiments, the needle 104 is a hollow hypodermic needle having a sharpened needle tip 106 used to facilitate catheterization. For example, in one embodiment, the sharpened needle tip 106 can include a V-point designed to reduce the penetration force used to penetrate the needle 104 and a portion of the catheter insertion assembly 102 through the skin, tissue, and vein wall of a patient.

Various types of catheter insertion devices 102 are marketed by Smiths Medical ASD, Inc. of St. Paul, Minn., under the JELCO trademark. One embodiment of a catheter insertion device 102 (such as that depicted in FIGS. 1 and 2) is described in U.S. Pat. Nos. 7,291,130 and 8,257,322 (depicting an IV catheter insertion device marketed by Smiths Medical ASD, Inc. under the INTUITIV trademark), both of which are incorporated by reference herein.

In other embodiments, the catheter insertion device 102 can provide a safety needle assembly (such as that depicted in FIGS. 3 and 4A-B) that functions to house the sharpened tip 106 of the needle 104 to reduce the likelihood of an inadvertent needle stick. Examples of this type of catheter insertion device 102 are depicted in U.S. Pat. No. 5,000,740 (depicting an IV catheter insertion device marketed by Smiths Medical ASD, Inc. under the PROTECTIV trademark), U.S. Pat. No. 7,736,342 (depicting an IV catheter insertion device marketed by Smiths Medical ASD, Inc. under the VIAVALVE trademark), both of which are incorporated by reference herein. In these embodiments, the catheter insertion device 102 is generally shiftable between an in use position (as depicted in FIG. 4A) in which the needle 104 is exposed such that the intravenous catheter assembly 100 can be positioned atop and/or coaxially ride over a portion of the needle 104 during catheterization, and a safe position (as depicted in FIG. 4B) in which the needle 104 is safely retracted within a portion of the catheter insertion device 102, thereby inhibiting the risk of an inadvertent needle stick.

In some embodiments, the catheter insertion device 102 can be a passive safety device, such that removal of the intravenous catheter assembly 100 from the catheter insertion device 102 is inhibited until the needle 104 is safely retracted and locked into a safe position. Release of the intravenous catheter assembly 100 from the catheter insertion device 102 may occur without additional actions performed by the clinician beyond the normal catheterization protocol. Examples of this type of catheter insertion device 102 are described in U.S. Patent Publ. No. 2016/0220791, filed Feb. 1, 2016, which is incorporated by reference herein.

II. Intravenous Catheter Assembly

Intravenous catheter assembly 100 generally includes a catheter tube 108 and a catheter hub 110. In some embodiments, the intravenous catheter assembly can further include one or more wings 112, an extension tube 114, an extension tube clamp 116, a needleless connector 118, and a vent cap 120. In some embodiments, the intravenous catheter assembly further includes a sheath 122 configured to fit over a portion of the intravenous catheter assembly 100 when coupled to the catheter insertion device 102.

A. Catheter Tube, Hub and Wings

Referring to FIGS. 5A-B the catheter tube 108 and catheter hub 110 are depicted in accordance with an embodiment of the disclosure. Catheter tube 108 can extend from a distal end 124 to a proximal end 126, where the catheter tube 108 can be operably coupled to the catheter hub 110. The catheter tube 108 can define a lumen 128 configured to provide a fluid pathway between the vein of a subject and the catheter hub 110. In one embodiment, the catheter tube 108 can include a barium radio opaque line to ease in the identification of the catheter tube 108 during radiology procedures.

Catheter hub 110 can include a catheter hub body 130, a septum 132 and a septum retainer 134. FIG. 6 depicts a perspective view of the catheter hub body 130 and a septum retainer 134 in accordance with an embodiment of the disclosure. Catheter hub body 130 can have a distal end 136, a proximal end 138, and an internal wall 140 defining a first internal fluid passageway 142 therebetween. In one embodiment, the distal end 136 of the catheter hub body 130 is operably coupled to the proximal end 126 of the catheter tube 108, such that the lumen 128 of the catheter tube 108 is in fluid communication with the first internal fluid passageway 142. In one embodiment, the internal wall 140 further defines a transition step 144 within the first internal fluid passageway 142 between a smaller diameter portion 146 of the first internal fluid passageway 142 proximal to the distal end 136, and a larger diameter portion 148 of the first internal fluid passageway 142 distal to the proximal end 138.

In one embodiment, the internal wall 140 further defines a side port 150. In one embodiment, the side port 150 is in fluid communication with the first internal fluid passageway 142. In one embodiment, the side port 150 extends away from the first internal fluid passageway 142 and at an oblique angle to the lumen 128 of the catheter tube 108. Side port 150 can provide a connection point to one or more lengths of extension tube 114, so that the inside of the extension tube 114 is in fluid communication with the first internal fluid passageway 142. In one embodiment, the internal wall can further include an extension tube connection point 152.

Septum 132 can have a distal end 154, a proximal end 156, and an outer perimeter 158. In one embodiment, the septum 132 is constructed of a flexible, fluid impermeable material. For example, the septum 132 can be constructed of silicone, isoprene, or other flexible materials. In one embodiment, the septum 132 is self-sealing, so that when the needle 104 is withdrawn through the septum 132, any void left by the withdrawn needle 104 will close to provide a fluid tight barrier, and the septum 132 will maintain its fluid impermeability. In one embodiment, the septum 132 is configured to provide a fluid tight seal under pressure injection in which the injected medicament can be pressurized to 300 psi or greater, up to 325 psi or greater, or up to 350 psi or greater, according to various example embodiments.

In one embodiment, the septum 132 is positioned partially within the first internal fluid passageway 142 proximal to the side port 150, such that the distal end 154 of the septum 132 abuts up against the transition step 144, thereby inhibiting forward movement of the septum 132 within the first internal fluid passageway 142. Septum 132 can be constrained about its outer perimeter 158 by the internal wall 140 of the catheter hub body 130. In one embodiment, the septum 132 is sized to fit within the first internal fluid passageway 142 to create a fluid tight seal with the internal wall 140 to inhibit fluid within the lumen 128 or the first internal fluid passageway 142 from escaping through the proximal end 138 of the catheter hub body 130. The septum may be radially compressed within the catheter hub body 130 to promote a seal with the catheter hub body and/or the insertion needle when present in the septum. According to some embodiments, the septum is compressed up to 10% by volume, up to 15% by volume, up to 20% by volume, or even greater. Rearward movement of the septum 132 can be restricted or inhibited by the septum retainer 134.

Septum retainer 134 can be configured to secure the septum 132 in position within the first internal fluid passageway 140. In one embodiment, the septum retainer 134 can have a distal end 160, a proximal end 162, an inner wall 164, and an outer wall 166 therebetween. Septum retainer 134 can be at least partially or fully insertable within the first internal fluid passageway 140 of the catheter hub body 130. In one embodiment, the proximal end 162 of the septum retainer 134 is flush with, or recessed with respect to the proximal end 138 of the catheter hub body 130. In one embodiment, the inner wall 164 defines a second internal passageway 168 such as can be used to accommodate an insertion needle of the catheter insertion device. In one embodiment, the outer wall 166 is shaped and sized to interlock with the internal wall 140 of the catheter hub body 130, thereby coupling the septum retainer 134 to the catheter hub body 130. In one embodiment, the outer wall 166 defines an aperture 170 configured to enable the needle 104 to pass therethrough.

In one embodiment, the septum retainer 134 is snap fit into the catheter hub body 130, without the use of adhesives or ultrasonic welding to couple the septum retainer 134 to the catheter hub body 130. To facilitate a snap fit, in one embodiment, the septum retainer 134 can include a circumferential retainer ridge 172 as a portion of the outer wall 166, such that the outer wall 166 and the circumferential retainer ridge 172 are shaped and sized to interlock with the internal wall 140 of the catheter hub body 130. In some embodiments, the internal wall 140 of the catheter hub body 130 can include a circumferential channel 174, configured to receive the circumferential retainer ridge 172 (depicted in FIG. 5B).

In one embodiment, the septum retainer 134 can further include a plurality of lateral ribs 176 positioned on the outer wall 166. Lateral ribs 176 can be configured to inhibit the septum retainer 134 from rotating relative to the catheter hub body 130 when the septum retainer 134 is assembled with the catheter hub body 130.

In one embodiment, the catheter hub body 130 can include one or more ledges 178 configured to provide support for one or more wings 112. In one embodiment, the ledges 178 can define one or more holes 180. The holes 180 can provide improved contact with the one or more wings 112, when the one or more wings 112 are integrally molded onto a portion of the catheter hub body 130. Accordingly, the ledges 178 can serve to both increase the bonding surface between the catheter hub 110 and the wings 112, as well as to serve as a partial structural reinforcement for the wings 112.

Wings 112 generally extend outwardly from the central axis of the catheter tube 108 and the catheter hub 110, so as to provide an adequate gripping surface for a clinician, as well as an extended surface for aid in securing the catheter hub 110 in place on the patient. In one embodiment, the wings 112 can be integrally molded onto a portion of the catheter hub 110. For example the wings 112 can be coupled to the catheter hub 104 via a collar 184 or the like, that at least partially surrounds the catheter hub 110.

In one embodiment, the wings 112 are constructed of a flexible material, thereby enabling the wings 112 to flex to accommodate the surface of the patient's skin. As best depicted in FIG. 5A, in one embodiment, the bottom surface 182 of the wings 112 can be sloped such that the catheter tube 108 can remain in a substantially straight-line configuration, without a significant bend or hinge point when the catheter tube 108 is inserted into a patient and the wings 112 are secured to the patient skin. Sloped bottom surface 182 enables the wings 112 to be substantially parallel to the skin of the patient, thereby increasing the surface contact between the one or more wings 112 and the patient's skin.

B. Extension Tube and Clamp

Referring to FIGS. 3-4B, an extension tube 114 and extension tube clamp 116 are depicted in accordance with an embodiment of the disclosure. In one embodiment, the extension tube 114 can be substantially transparent or translucent to enable the observation of fluid within the extension tube 114. In one embodiment, the extension tube clamp 116 can be constructed of a resilient material that can be deformed to selectively occlude the extension tube 114 to restrict the passage of fluid.

C. Needleless Connector

Referring to FIGS. 7A-C, a needleless connector 118 is depicted in accordance with an embodiment of the disclosure. In one embodiment, the needleless connector 118 is configured to connect the extension tube 114 to a connector of an IV fluid supply line, as partially shown in FIG. 7C. In one embodiment, the needleless connector 118 includes a Luer lock connector 119 for connection to an IV fluid supply line. In one embodiment, the needleless connector 118 is a needle-free connector, for example the connector described in U.S. Pat. No. 7,713,248 (depicting a needle-free connector marketed by ICU Medical, Inc. under the CLAVE trademark), which is hereby incorporated by reference.

In one embodiment, the needleless connector 118 is comprised of a conical internal conduit 188 with one or more fluid path windows 190, a flexible compression seal 192 capable of selectively covering the internal conduit 188, and a housing 194 substantially surrounding the internal conduit 188 and the compression seal 192. Needleless connector 118 can inhibit the escape of bodily fluid and/or guard against contamination of the fluid path. As depicted in FIG. 7B, in the uncompressed state, the compression seal 192 extends over the fluid path windows 190 of the internal conduit 188, thereby creating a fluid seal to inhibit fluid from escaping from the extension tube 114. Conversely, as depicted in FIG. 7C, when an IV fluid supply connector 186 is inserted into the housing 194, the compression seal 192 is shifted to a compressed state, thereby exposing the fluid path windows 190 to the fluid path of the IV fluid supply connector 186. Accordingly, the needleless connector 118 selectively enables the flow of fluid through the extension tube 114, while both sealing the intravenous catheter assembly 100 from the ambient environment and inhibiting the escape of bodily fluid from a patient when the IV fluid supply connector 186 is not attached.

Needleless connector 118 thus enables the intravenous catheter assembly 100 to act as a closed system when not connected to either the catheter insertion device 102 or an IV fluid supply connector 186. That is the needleless connector 118, in combination with various embodiments of the vent cap described herein, inhibit bodily fluid, such as blood, from escaping from the intravenous catheter assembly 100 until an IV fluid supply 186 (or other similar type device) is connected. Additionally, the interior portions of the needleless connector 118 and the extension tube 114 are protected from exposure to the ambient environment. By contrast, many conventional designs (such as that depicted in FIGS. 1 and 2) employ a flash plug that is assembled to the extension tube of a catheter insertion device during catheter insertion. Prior to connecting the intravenous catheter assembly to an IV supply, a clamp 38 designed to crimp the extension tube 36 is engaged to inhibit bodily fluid from flowing freely from the patient when the flash plug is removed. However, bodily fluid that is present in the extension tube between the clamp and the proximal end of the extension tube may escape from the catheter assembly, at least until the IV supply is connected to the catheter assembly.

During or after catheter insertion with the catheter tube 108 inserted into the patient's vein, blood or bodily fluid from a patient enters the catheter tube 108 and other portions of the intravenous catheter assembly 100, purging air from within the intravenous catheter assembly 100, either through a gas porous barrier of the catheter insertion device or the needleless connector, when activated by a vent cap 120. In some embodiments, the compression seal 192 can be shipped with a vent cap 120 assembled thereto in an activated or open/venting configuration. However, it has been found that extended compression of the compression seal 192 of some needleless connector 118 embodiments can cause the compression seal 192 to permanently deform. Accordingly, some example embodiments are configured with a vent cap 120 that can be assembled to the needleless connector in a first, initial position where the vent cap 120 is retained by the needleless connector with the needleless connector in a closed state where deformation of the compression seal is avoided. Prior to catheter insertion, the vent cap 120 can be moved or shifted to a second position to compress the compression seal, thereby opening the needleless connector and enabling air to be purged from the intravenous catheter assembly. The vent cap 120 may include an air permeable barrier that inhibits the escape of bodily fluids, such as blood, while permitting the escape of air, as is described in greater detail herein.

Figure 8:
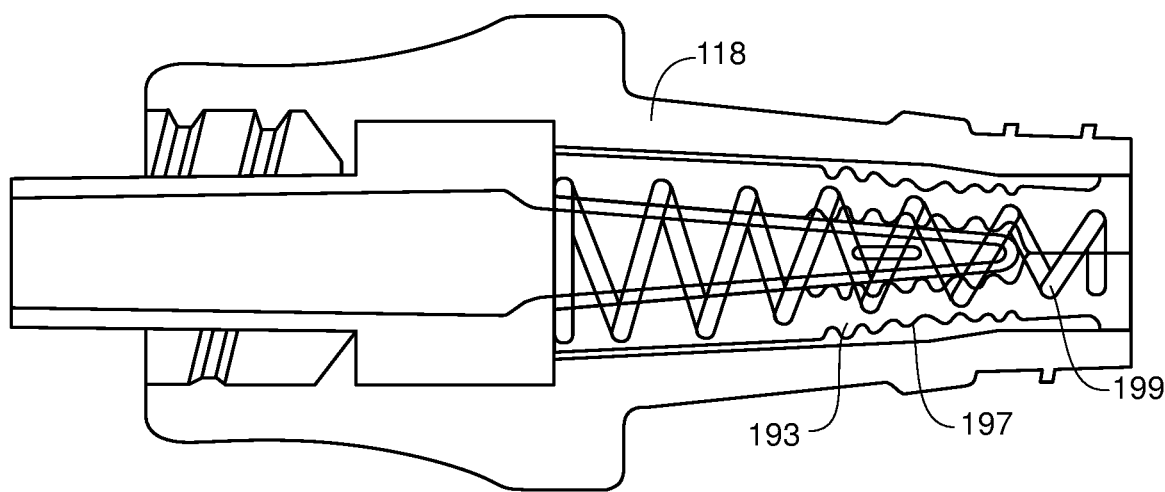
FIG. 8 is a cross sectional view depicting a needleless connector having a spring configured to bias a compression seal to a closed position in accordance with an embodiment of the disclosure.

Referring to FIG. 8, in one embodiment, the needleless connector 118 includes an improved compression seal 193. Improved compression seal 193 can include additional bellows 197, additional material and/or a coil spring 199 configured to counteract the tendency of the needleless connector 118 to permanently deform when the improved compression seal 193 has been compressed for a duration of time consistent with the amount of time that an intravenous catheter assembly may be in storage prior to use, such as up to 1 year, up to 2 years, up to 3 years, or event up to 5 years or more.

Figure 9:
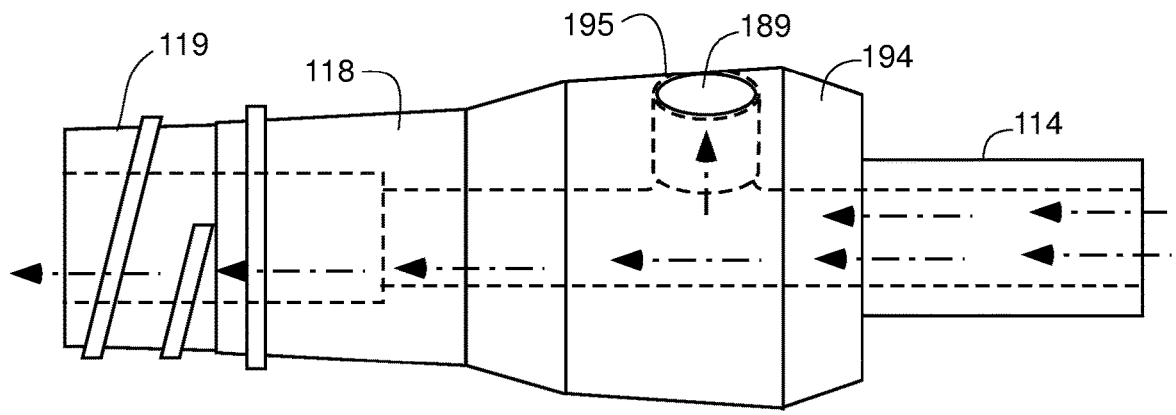
FIG. 9 is a profile view depicting a needleless connector including an air permeable barrier in accordance with an embodiment of the disclosure.

Referring to FIG. 9, in one embodiment, the needleless connector 118 can include a vent 189 residing within a vent aperture 195 defined within housing 194. Vent 189 can be comprised of an air permeable membrane that enables air or gas to vent as blood or bodily fluid fills the interior of the needleless connector 118, but inhibits the blood or bodily fluid from passing entirely through the vent 189. In this embodiment, blood or bodily fluid from the patient provides pressure to push the trapped gas through the vent 189, and out of the intravenous catheter assembly 100. Accordingly, vent 189 enables venting of gas trapped within the intravenous catheter assembly 100 upon insertion of the catheter tube 108 into a patient's vein, without additional user input on behalf of the clinician.

Figure 10A:
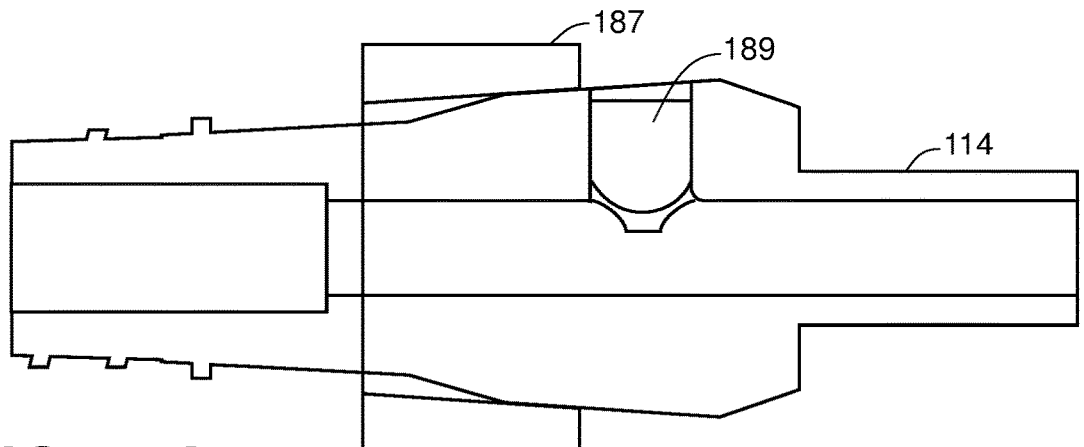
FIG. 10A is a profile view depicting a needleless connector including an air permeable barrier and a seal ring in accordance with an embodiment of the disclosure, wherein the seal ring is in a first, venting position.
Figure 10B:
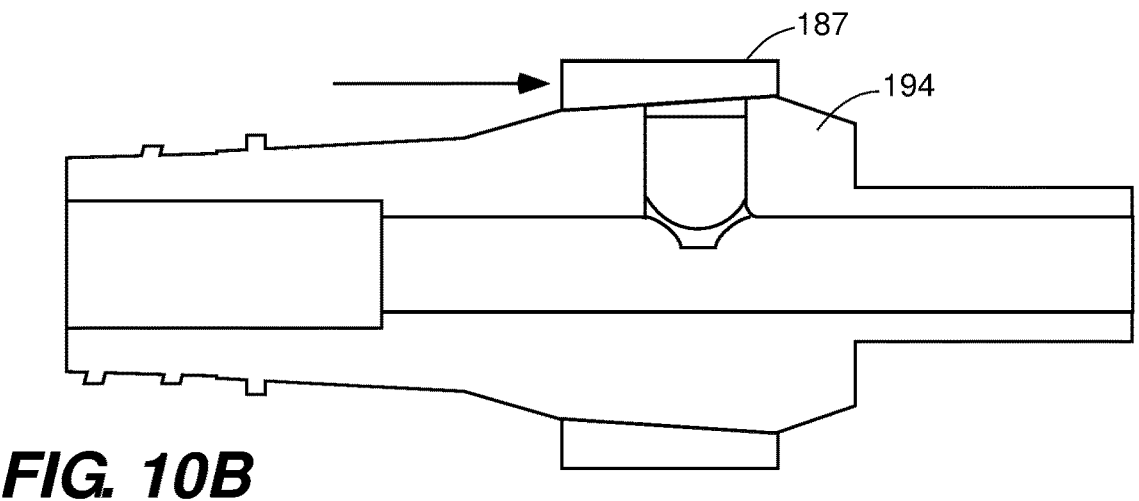
FIG. 10B is a profile view depicting the needleless connector of FIG. 10A, wherein the seal ring is in a second, vent sealing position.

Referring to FIGS. 10A-B, in one embodiment, the needleless connector 118 further includes a seal ring 187. Seal ring 187 can be configured to shift from a first, initial position (as depicted in FIG. 10A), in which vent 189 is exposed to the ambient environment, to a second, vent sealing position (as depicted in FIG. 10B), in which vent 189 is at least partially covered or shielded by the sealing ring 187, thereby restricting further venting and/or serving to protect the vent 189 from external forces. In one embodiment, the sealing ring 187 is shifted from the first, initial position to the second, vent sealing position by the connection of an IV fluid supply line 186 to the Luer lock connector 119. In one embodiment, the sealing ring 187 and the housing 194 are configured to mate by an interference and/or snap fitting when in the second, vent sealing position, thereby restricting movement of the sealing ring 187 back to the first, initial position.

Figure 11A:
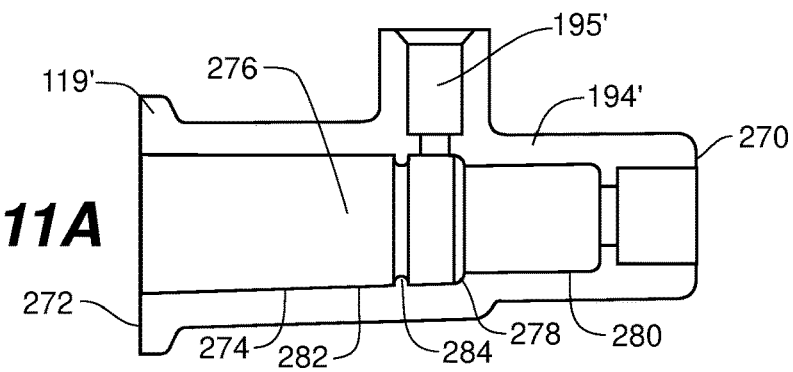
FIG. 11A is a cross sectional view depicting a housing of a needleless connector in accordance with an embodiment of the disclosure.

Referring to FIGS. 11A-D, a second embodiment of a needleless connector 118' is depicted in accordance with an embodiment of the disclosure. In this embodiment, the needleless connector 118' can include a housing 194'. As depicted in FIG. 11A, the housing 194' can have a distal end 270, a proximal end 272 and an internal wall 274 defining an internal fluid passageway 276 therebetween. The internal wall 274 can define a vent aperture 195'. Vent aperture 195' can be shaped and sized to accommodate a vent 189' there within. Vent 189' can include an air permeable membrane that enables air or gas to vent as blood or bodily fluid fills the internal fluid passageway 276 of the needleless connector 118', but inhibits the blood or bodily fluid from passing entirely through the vent 189'.

In one embodiment, the internal wall 274 further defines a transition step 278 within the internal fluid passageway 276 between a smaller diameter portion 280 and a larger diameter portion 282 of the internal fluid passageway 276 proximal to the distal end 270. The internal wall 274 can further define a circumferential ridge 284 positioned proximately to the transition step 278.

Figure 11B:
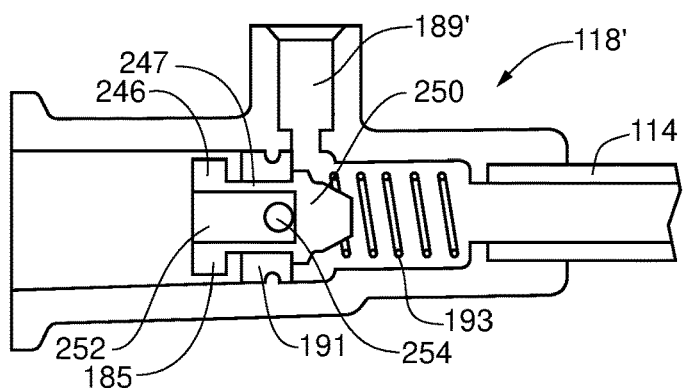
FIG. 11B is a cross sectional view depicting a needleless connector coupled to an extension tube in accordance with an embodiment of the disclosure, wherein the needleless connector includes a shiftable spool valve in the venting position.

As depicted in FIG. 11B, the distal end 270 of the housing 194' can be operably coupled to a proximal end of the extension tube 114, such that the extension tube 114 is in fluid communication with the first internal fluid passageway 276. In one embodiment, the proximal end 272 can define a Luer lock connector 119' configured for connection to an IV fluid supply line 186.

Figure 11C:
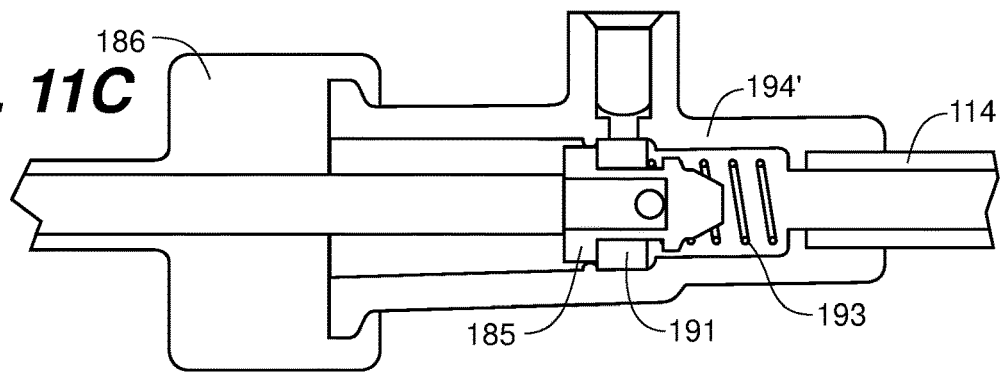
FIG. 11C is a cross sectional view depicting the needleless connector of FIG. 11A coupled to an IV fluid supply, wherein the spool valve is shifted to the open position.
Figure 11D:
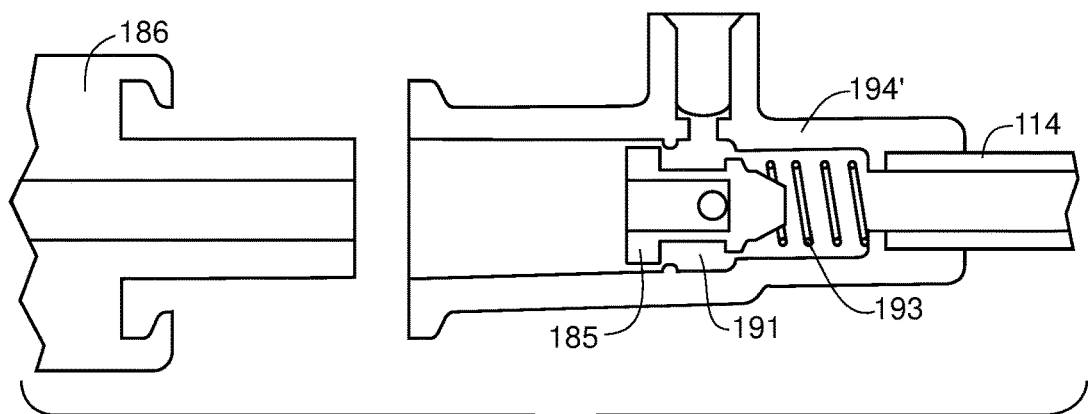
FIG. 11D is a cross sectional view depicting the needleless connector of FIG. 11B uncoupled from the IV fluid supply, wherein the spool valve is shifted to the closed position.

Needleless connector 118' can further include a spool valve 185, a seal 191 and a coil spring 193. Spool valve 185, seal 191 and coil spring 193 can be movable relative to the housing 194' between an initial, venting position (as depicted in FIG. 11B), an IV fluid supply line open position (as depicted in FIG. 11C), and a closed position (as depicted in FIG. 11D). In particular, the spool valve 185 can shift the seal 191 from the initial, venting position to a vent closed position relative to the housing 194'. The spool valve 185 can then shift relative to the seal 191 between the IV fluid supply line open position and the closed position.

In one embodiment, the spool valve 185 can include a base portion 246 shaped and sized to fit within the housing 194', such that spool valve 185 can shift relative to the housing 194'. Spool valve 185 can include a neck portion 247, configured to shiftably couple with the seal 191, such that the seal 191 can shift along the neck portion 247 relative to the spool valve 185 between a distal position (as depicted in FIGS. 11B and 11D) and a proximal position (as depicted in FIG. 11C). Spool valve 185 can include a head portion 250 operably coupled to the coil spring 193.

Seal 191 can be configured as a ring that fits around the neck portion 247 of the spool valve 185. In some embodiments, the seal 191 can be constructed of an elastomer or of another flexible, resilient material capable of sealing vent 189'. Seal 191 can be configured to provide a fluid tight seal against the neck portion 247 and/or a proximal portion of the head portion 250 and/or a distal portion of the base portion 246 of the spool valve, as well as the internal wall 274 of the internal fluid passageway 276. In one embodiment, an outer diameter of the seal 191 can vary. For example, the distal and proximal ends of seal 191 can have a larger diameter, while a portion between the distal and proximal ends can have a smaller diameter, thereby enabling proper sealing against internal wall 274, while minimizing frictional resistance during shifting.

Spool valve 185 can define an axially aligned blind bore 252 extending from the base portion 246 towards the neck portion 247, but terminating internally proximal to the head portion 250, so as to not penetrate all of the way through the spool valve 185. Spool valve 185 can further define one or more fluid supply apertures 254 passing from the outer surface of the spool valve 185 proximal to the neck portion 247 and terminating at the blind bore 252. In one embodiment, the one or more fluid supply apertures 254 are substantially orthogonal to the axially aligned blind bore 252.

In the initial, venting position (as depicted in FIG. 11B), the seal 191 can be positioned proximal to the vent aperture 195 and can cover the one or more fluid supply apertures 254. In one embodiment, the seal 191 can be at least partially held in the initial, venting position by interference with the circumferential ridge 284. In this configuration, air or gas trapped within the intravenous catheter assembly 100 is able to vent through the vent aperture 195' upon insertion of the catheter tube 108 into a patient's vein, with no additional user input required by a clinician.

Upon connection of the needleless connector 118' to an IV fluid supply line 186, the spool valve 185 can be forced distally by the IV fluid supply line 186, such that the seal 191 initially shifts relative to the spool valve 185 along the neck portion 248 to a proximal position, so as to make contact with the base portion 246 and uncover the fluid supply apertures 254. As the spool valve 185 is shifted distally, the coil spring 193 compresses. Upon making contact with the base portion 246, further distal movement of the spool valve 185 causes the seal 191 to shift distally, so as to cover the vent aperture 195' (as depicted in FIG. 11C). In one embodiment, the seal 191 is configured to provide a fluid tight seal around both the neck portion 248 and/or a distal portion of the base portion 246, thereby enabling the flow of fluid through the fluid supply apertures 254 of the spool valve 185. In this configuration, a fluid supply coming from IV fluid supply connector 186 can pass through fluid supply apertures 254 and into extension tube 114.

Upon disconnection and removal of the IV fluid supply connector 186 from the needleless connector 118', the coil spring 193 forces the spool valve 185 to shift proximately relative to both the housing 194' and to the seal 191, thereby causing the seal 191 to occlude the fluid supply apertures 254 (as depicted in FIG. 11D). In one embodiment, seal 191 is configured to provide a fluid tight seal around both the neck portion 248 and/or a proximal portion of the head portion 250, thereby inhibiting the flow of fluid through spool valve 185. In this configuration, the needleless connector 118' is closed, such that the seal 191 restricts fluid communication between extension tube 114 and both the vent aperture 195' and the one or more fluid supply apertures 254.

D. Vent Cap

Figure 12A:
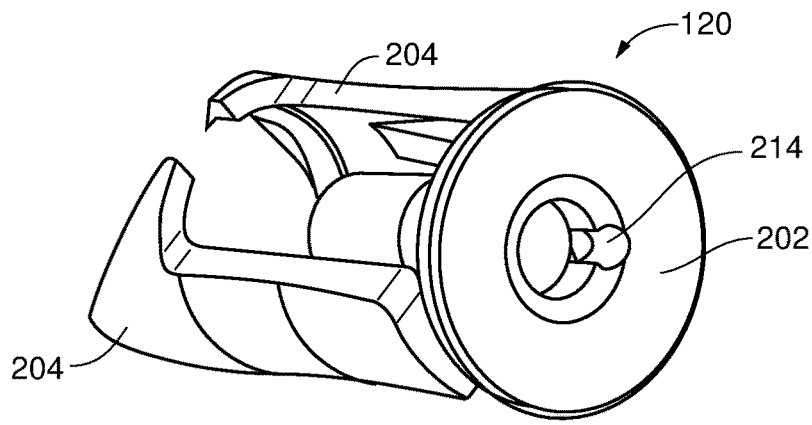
FIG. 12A is a perspective view depicting a vent cap in accordance with an embodiment of the disclosure.
Figure 12B:
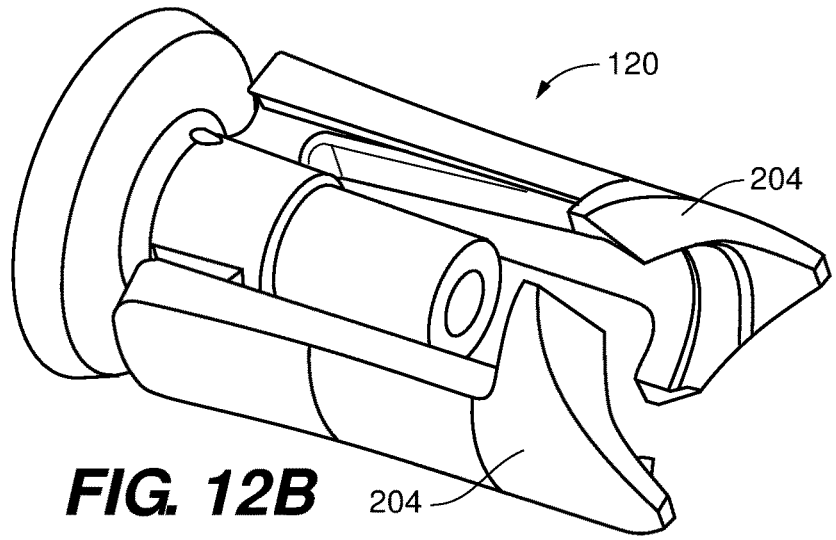
FIG. 12B is another perspective view depicting the vent cap of FIG. 12A.
Figure 12C:
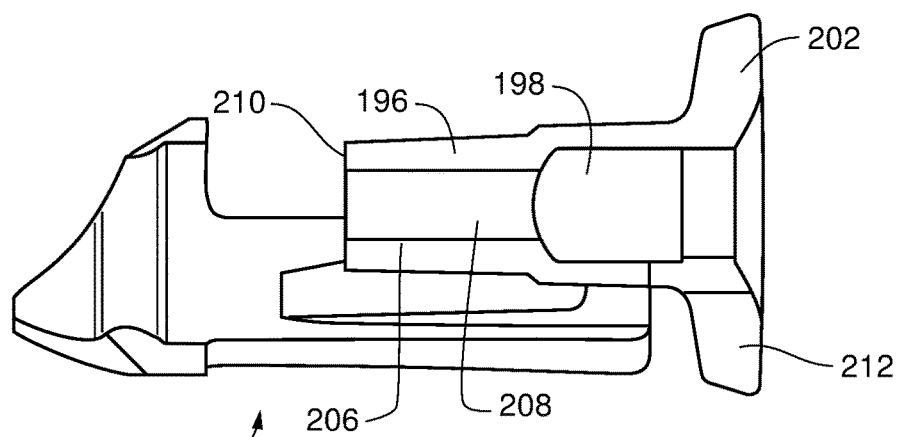
FIG. 12C is a sectional view depicting the vent cap of FIG. 12A.

Referring to FIGS. 12A-C, various views of a vent cap 120 in accordance with an embodiment of the disclosure are depicted. One function of the vent cap 120 is to shift the compression seal 192 to the compressed state when an IV fluid supply line 186 is not attached to the needleless connector 118, for the purpose of venting gas trapped within the intravenous catheter assembly 100 while preventing the escape of blood. In particular, under normal conditions, bodily fluid from a patient in which the catheter tube 108 has been inserted can provide the necessary pressure to push the trapped gas through the vent cap 120. In some embodiments, the vent cap 120 can be disposed of after use.

In one embodiment, the vent cap 120 can include a nose 196, a flash plug 198, a push plate 202, and one or more needleless connector engagement arms 204. Nose 196 can be sized and shaped to fit within the housing 194 of the needleless connector 118 in place of the IV fluid supply connector 186. In some embodiments, the nose 196 can be tapered. Nose 196 can include a vent path wall 206 defining a vent path 208. The vent path 208 can have a diameter sufficient to receive the portion of internal conduit 188 that would otherwise extend into the IV supply connector, such that the fluid path windows 190 of the needleless connector 118 at least partially reside within the vent path 208. A distal end 210 of the nose 96 can be in abutting contact with the compression seal 192 and can provide a fluidic seal therebetween.

Figure 13A:
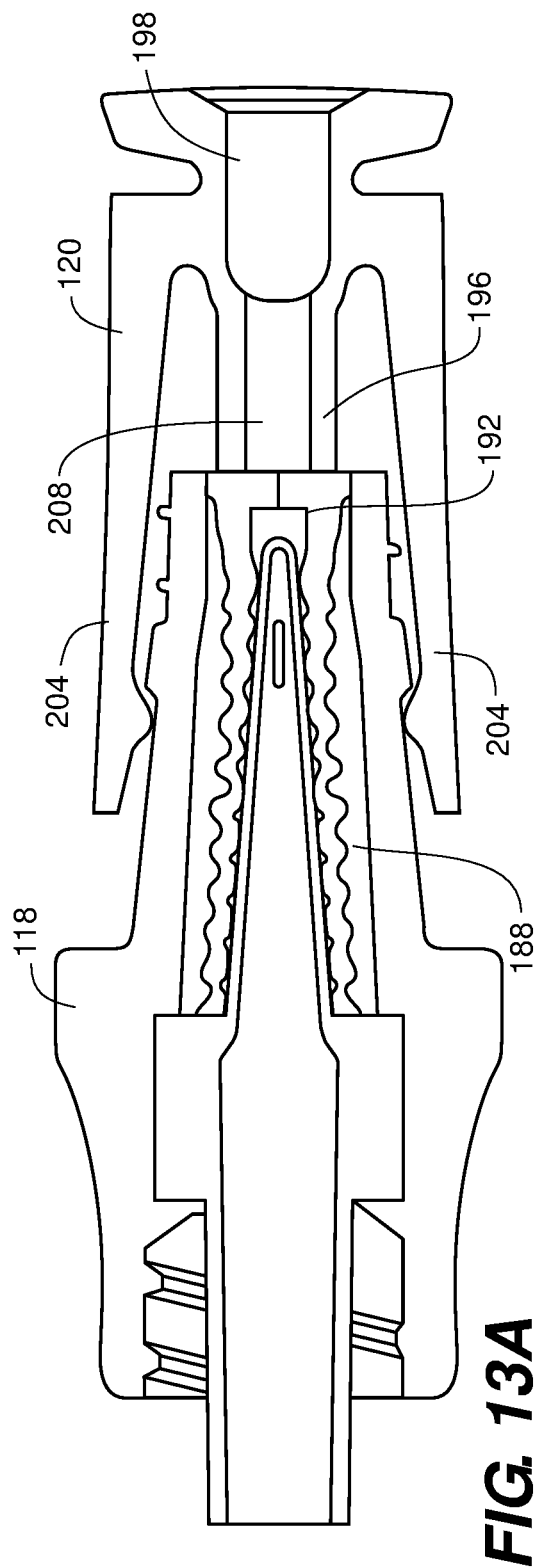
FIG. 13A is a cross-sectional view depicting a vent cap and needleless connector in accordance with an embodiment of the disclosure, wherein the vent cap is in a first, storage position relative to the needleless connector.
Figure 13B:
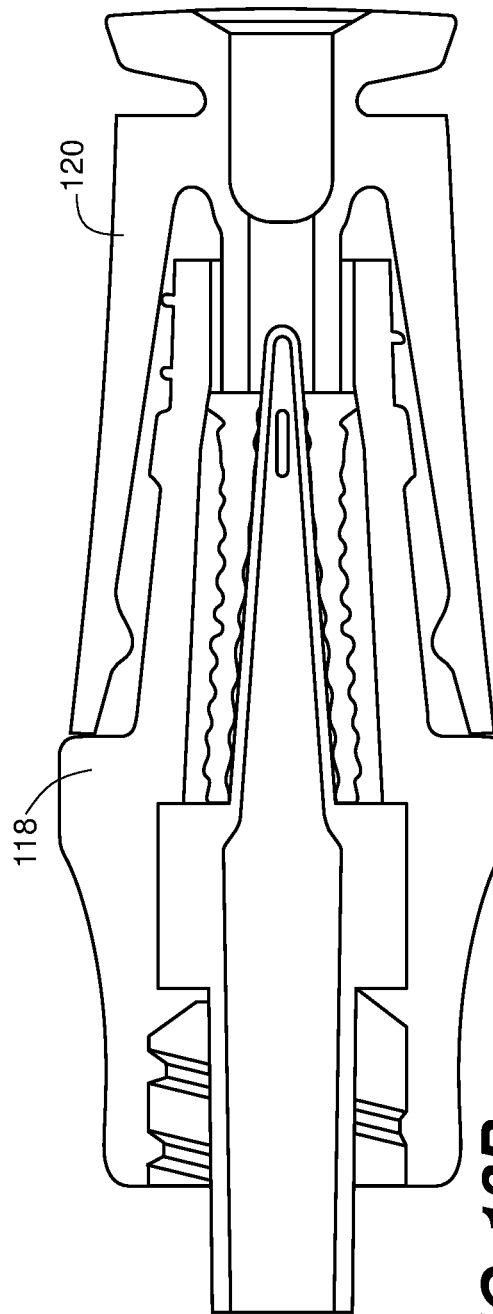
FIG. 13B is a cross sectional view depicting the vent cap and needleless connector of FIG. 13A, wherein the vent cap is in a second, actively depressed position relative to the needleless connector.

Referring to FIGS. 13A-B, the vent cap 120 can be assembled to a needleless connector and movable or shiftable between a first, storage position (as depicted in FIG. 13A), in which the compression seal 192 of the needleless connector 118 is in an uncompressed state, thereby inhibiting fluid from passing through the vent path 208, and a second, actively depressed position (as depicted in FIG. 13B), in which the compression seal 192 of the needleless connector 118 is in a compressed state, thereby permitting fluid to pass through vent path 208.

Air permeable barrier 198 can be positioned within a portion of the vent path 208. Air permeable barrier 198 can be comprised of an air permeable matrix that enables air or gas to vent as blood or bodily fluid fills the vent path 208, but inhibits the blood or bodily fluid from passing entirely through the vent path 208. In some embodiments, the vent cap 120 can be constructed of a transparent or translucent material. During the venting of air, blood or other bodily fluid can fill a portion of the vent path 208, thereby providing a visual confirmation to the clinician that the catheter tube 108 has been inserted into a patient's vein. Such visual confirmation can be referred to as secondary flashback, wherein a primary flashback occurs in one or more flashback indicators located on the catheter insertion device 102.

Nose 196 can terminate in a push plate 202. Push plate 202 can include a flange 212 configured to provide a surface area for a clinician or user to push on as the vent cap 120 is manually shifted between the first, storage position and the second, actively depressed position. In one embodiment, a portion of the vent path wall 206 can further define an eyelet 214. Eyelet 214 can be configured to provide a fluid path for venting air between the vent path 208 and an exterior of the vent path wall 206. In particular, the eyelet 214 can provide a path for escaping air in the event that the clinician or user seals the end of the vent path 208 with their finger as the vent cap 120 is shifted to the second, actively depressed position.

The one or more needleless connector engagement arms 204 can be configured to grip a portion of the needleless connector 118. In some embodiments, the needleless connector engagement arms 204 can be constructed of a resilient material, such that the needleless connector engagement arms 204 tend to regain their original shape after temporary deformation. In some embodiments, the resiliency of the needleless connector arms 204 enables the vent cap 120 to be biased to the first, storage position when coupled to the needleless connector 118. In some embodiments, the outer surface of the housing 194 of the needleless connector 118 can be tapered to increase in diameter, such that when the vent cap 120 is shifted to the second, actively depressed position, the needleless connector engagement arms 204 are deflected away from one another. When the clinician or user releases the vent cap 120, the resiliency of the needleless connector engagement arms 204 can bias the vent cap 120 back to the first, storage position. In some embodiments, biasing the vent cap 120 to the first, storage position reduces the likelihood that the compression seal 192 of the needleless connector 118 will permanently deform, as can occur when the compression seal 192 is compressed for long periods of time, for example during storage.

Figure 14:
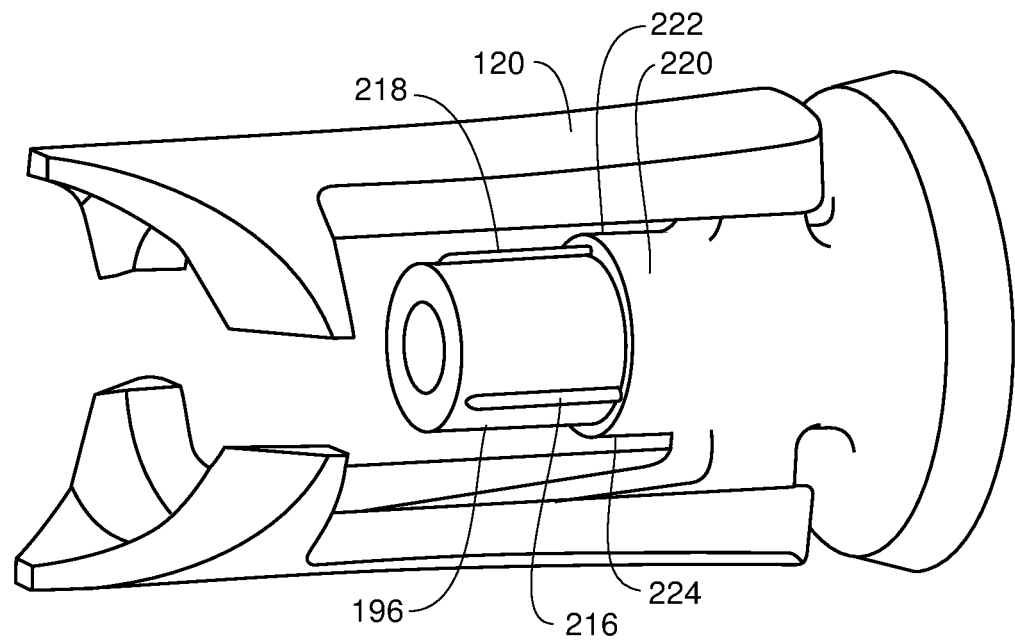
FIG. 14 is a perspective view of a vent cap having an un-tapered nose in accordance with an embodiment of the disclosure.
Figure 15:
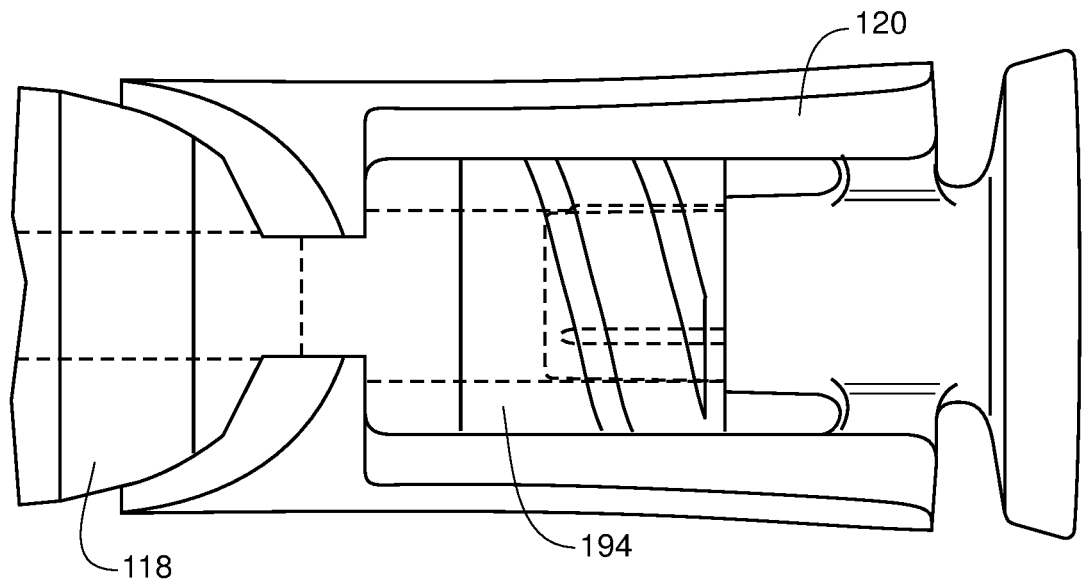
FIG. 15 is a profile view depicting the vent cap of FIG. 14 in the actively depressed position relative to a needleless connector.

Referring to FIGS. 14 and 15, in one embodiment, the nose 196 can have a first portion 218 and a second portion 220, with a transition step 222 positioned therebetween. First portion 218 can have a substantially constant outer diameter, as opposed to a taper, which can be present in other embodiments. One or more ribs 216 can be positioned along the outer surface or diameter of the first portion 218. For example, in one embodiment three ribs 216 can be substantially equally spaced apart around the outer diameter of the first portion 218. Ribs 216 can be configured to provide frictional interference with an internal surface of the housing 194 of the needleless connector 118, such that the user receives a tactile positive indication that the first portion 218 has fully entered into the housing 194 of the needleless connector 118, such that gas can be vented. With the substantially constant outer diameter of first portion 218, the force that a user applies to shift the vent cap 120 between the first, storage position and the second, actively depressed position remains substantially constant.

Second portion 220 can have a larger diameter than the first portion 218. Transition step 222 can be positioned between the first portion 218 and the second portion 220, and can include a surface 224 configured to make abutting contact with the housing 194 of the needleless connector 118 when shifted to the second, actively depressed position (as depicted in FIG. 15), so as to create a fluid tight barrier between the interior of the housing 194 and the ambient environment. In particular, the transition step 222 can be positioned at a location on the nose 196 where venting of the needleless connector 118 can occur, without causing damage to the internal conduit 188 or compression seal 192 of the needleless connector 118.

Figure 16:
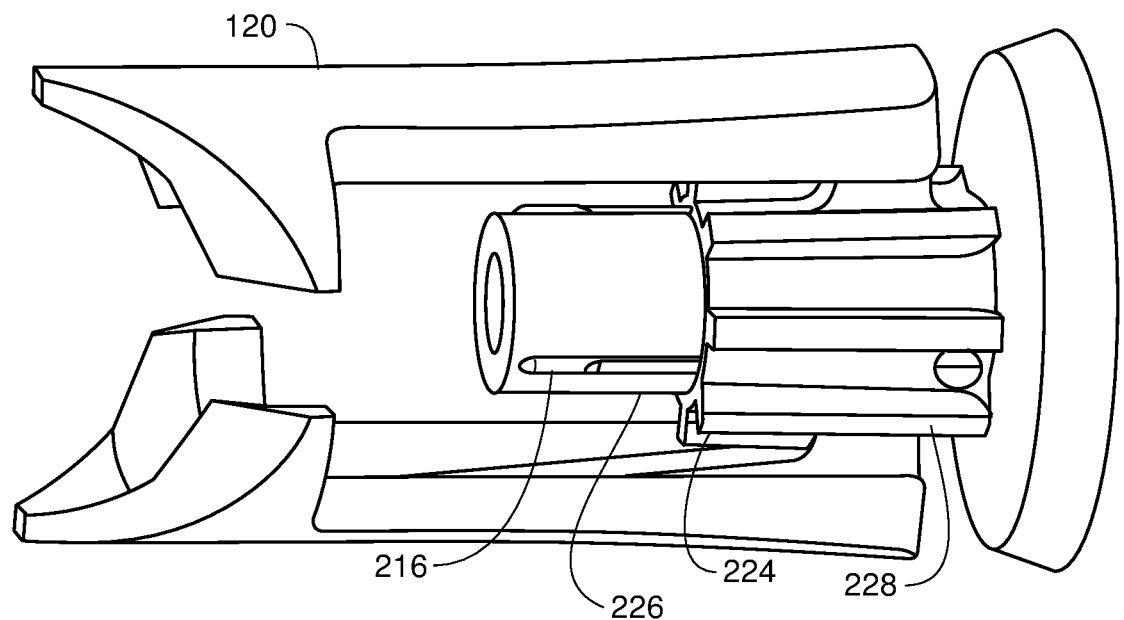
FIG. 16 is a perspective view of a vent cap having a reverse tapered nose or step in accordance with an embodiment of the disclosure.
Figure 17:
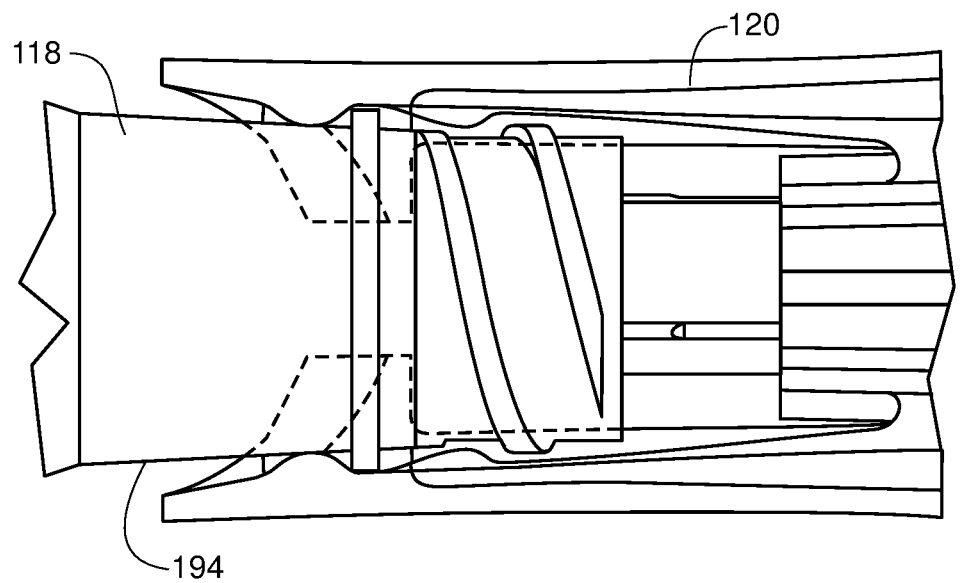
FIG. 17 is a profile view depicting the vent cap of FIG. 16 in the storage position relative to a needleless connector.

Referring to FIGS. 16 and 17, in one embodiment, the ribs 216 can include a portion 226 with a lower profile than other portions of the rib 216. In some embodiments, the portion 226 can include a reverse taper or other feature that causes the force used to move the vent cap 120 from the first, storage position (as depicted in FIG. 17) to the second, actively depressed position to reach an over center point and decreases thereafter as the vent cap approaches the second, actively depressed position. In some embodiments, the portions 226 of ribs 216 can be configured such that the vent cap 120 audibly snaps into the second, actively depressed position. In particular, a sudden contact between surface 224 and the housing 194 of the needleless connector 118 can be the source of an audible click and/or provide tactile feedback, wherein the configuration of the portions 226 enables the sudden contact. In one embodiment, the vent cap 120 can further include sound bars 228, configured to improve the audible clicking sound to positively indicate that the vent cap 120 has been shifted to the second, actively depressed position, and that any gaseous fluid trapped within the intravenous catheter assembly 100 has been vented.

Figure 18:
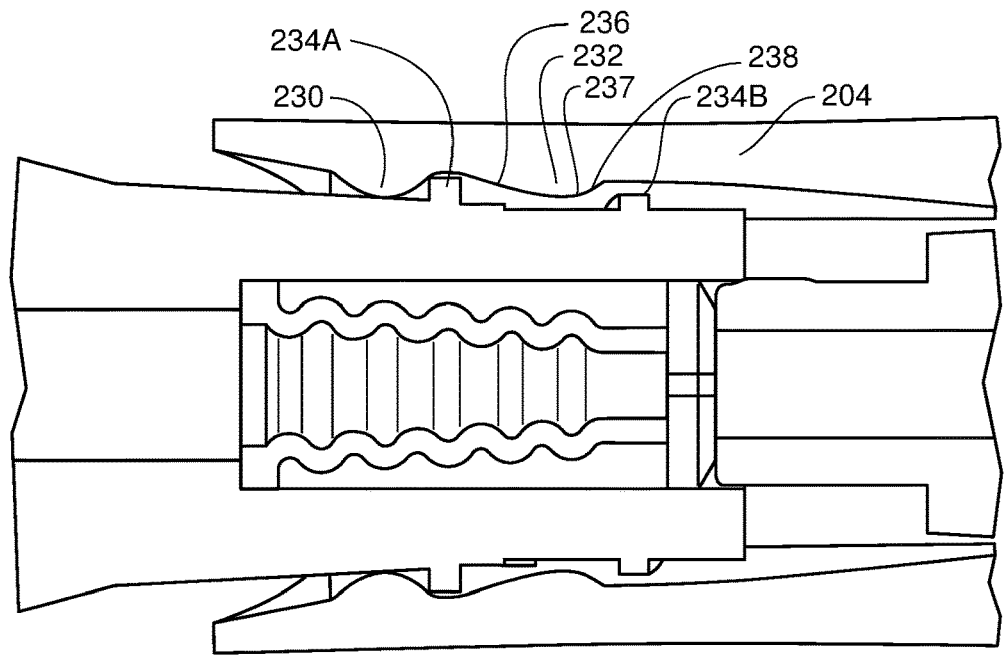
FIG. 18 is a partial cross sectional view of a needleless connector and needleless connector engagement arms of a vent cap in accordance with an embodiment of the disclosure, wherein the needleless connector engagement arms have a series of bumps configured to engage the needleless connector.
Figure 19A:
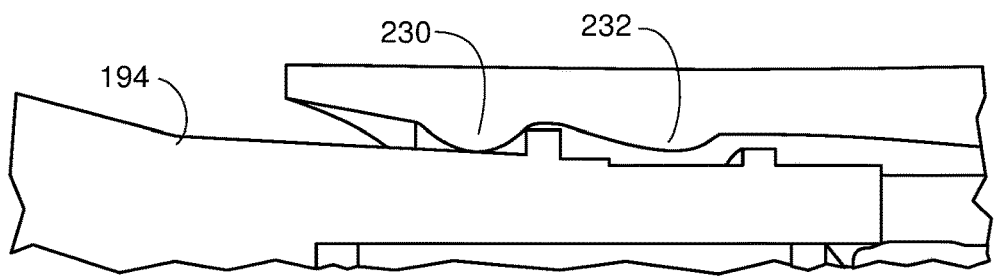
FIG. 19A is a fragmentary, close-up view depicting one of the needleless connector engagement arms of FIG. 18, wherein the vent cap is in the storage position relative to the needleless connector.
Figure 19B:
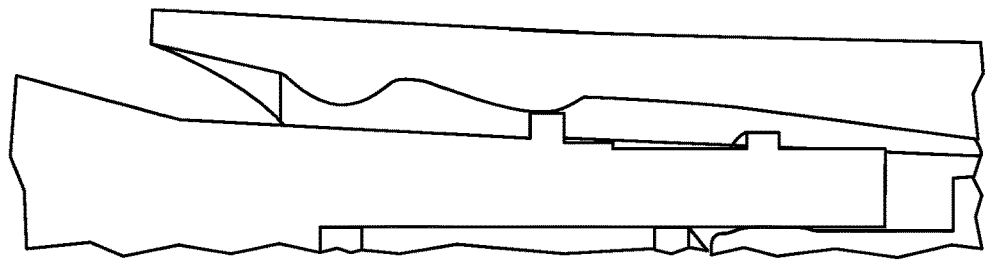
FIG. 19B is a fragmentary, close-up view depicting one of the needleless connector engagement arms of FIG. 18, wherein the vent cap is between the storage position and the actively depressed position relative to the needleless connector.
Figure 19C:
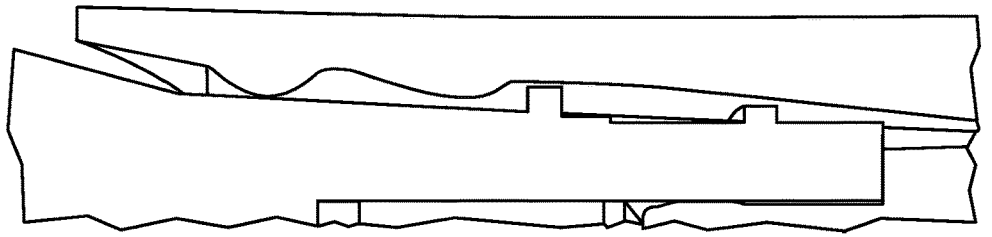
FIG. 19C is a fragmentary, close-up view depicting one of the needleless connector engagement arms of FIG. 18, wherein the vent cap is in the actively depressed position relative to the needleless connector.

Referring to FIGS. 18-19C, in one embodiment, the needleless connector engagement arms 204 can include a first bump 230 and a second bump 232. First bump 230 can be configured to grip the exterior of the housing 194 of the needleless connector 118, particularly when in the first, storage position. In some embodiments, the housing 194 can include one or more circumferential rings 234A/B, thereby enabling the needleless connector engagement arms 204 to positively grip the housing 194.

Second bump 232 can include a first sloped portion 236, a crest 237 and a second sloped portion 238. In one embodiment, the first sloped portion 236 can have a relatively shallow slope when compared to the second sloped portion 238, such that when the vent cap 120 is shifted from the first, storage position (as depicted in FIG. 19A), to the second, actively depressed position (as depicted in FIG. 19C), the relatively shallow slope of the first sloped portion 236 enables the needleless connector engagement arm 204 to flex to oppose the natural bias of the needleless connector engagement arms 204, such that the crest 237 rests on the top of the circumferential ring 234 (as depicted in FIG. 19B). Further movement of the vent cap 120 to the second, actively depressed position shifts the crest 237 forward, such that the relatively steeper slope of the second sloped portion 238 is positioned on top of the circumferential ring 234. The bias of the needleless connector engagement arms 204 in combination with the steeper slope of the second sloped portion 238 significantly reduces the force used to move the vent cap 120 to the second, actively depressed position. In this embodiment, the reduction in force can enable the needleless connector engagement arms 204 to rapidly move to their biased position against the surface of the housing 194, thereby creating an audible clicking sound. This audible clicking sound can be a positive indication to a user that the vent cap 120 has been shifted to the second, actively depressed position, and that any gaseous fluid trapped within the intravenous catheter assembly 100 has been vented.

Referring to FIGS. 20-21B, in one embodiment, the vent cap 120 can include two needleless connector engagement arms 204A/B coupled together by one or more breakable joints 240. For example, in one embodiment, the one or more breakable joints 240 can be a thin layer of the same material from which needleless connector engagement arms 204A/B are constructed. Breakable joints 240 can operably couple needleless connector engagement arms 204A/B together when in the first, storage position (as depicted in FIG. 21A), and can be broken when the vent cap 120 is moved to the second, actively depressed position (as depicted in FIG. 21B), when the needleless connector engagement arms 204A/B flex apart from one another. In one embodiment, the breakable joints 240 can be broken with the normal amount of force to transition or shift the vent cap 120 from the first, storage position to the second actively depressed position. In some embodiments, the breaking of breakable joints 240 creates an audible clicking sound and/or tactile feedback, thereby providing a positive indication to a user that the vent cap 120 has been shifted to the second, actively depressed position.

Referring to FIGS. 22-23B, in one embodiment, the vent cap 120 can include two needleless connector engagement arms 204A/B coupled together by one or more couplings 242. For example, in one embodiment, the one or more couplings 242 can be opposing hooks constructed from the same material from which the needleless connector engagement arms 204A/B are constructed. Couplings 242 can operably couple needleless connector engagement arms 204A/B together when in the first, storage position (as depicted in FIG. 23A), and can be uncoupled when the vent cap 120 is moved to the second, actively depressed position (as depicted in FIG. 23B), thereby enabling the needleless connector engagement arms 204A/B to flex apart from one another. In one embodiment, the coupling 242 can be uncoupled with the normal amount of force used to transition or shift the vent cap 120 from the first, storage position to the second actively depressed position. In some embodiments, the uncoupling of coupling 242 creates an audible clicking sound, thereby providing a positive indication to a user that the vent cap 120 has been shifted to the second, actively depressed position.

Figure 24:
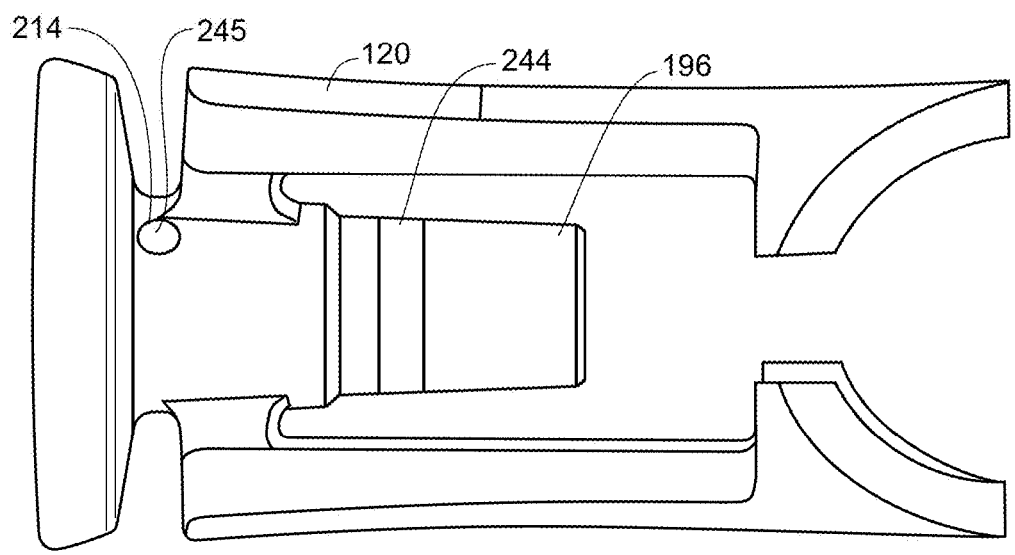
FIG. 24 is a profile view depicting a vent cap having a colored band in accordance with an embodiment of the disclosure.

Referring to FIG. 24, in one embodiment, the vent cap 120 can include one or more visual indicators, such as colored bands 243. Colored band 243 can be positioned on the nose 196 of the vent cap 120, such that when the vent cap 120 is shifted to the second, actively depressed position, the colored band 243 is completely or partially covered by the housing 194 of the needleless connector 118. In this embodiment, the colored band 243 can provide a visual indication of the position of the vent cap 120 relative to the needleless connector 118. In particular, the view of the colored band 243, which can be brightly colored, can be occluded by the housing 194 when the vent cap is shifted to the second, actively depressed position, thereby providing a visual indication that the vent cap 120 has been fully shifted.

In another embodiment, at least a portion of the housing 194 of the needleless connector 118 can be constructed of a transparent or translucent material having a color, such that when the vent cap 120 is shifted to the second, actively depressed position, the colored band 243 is positioned underneath the transparent or translucent portion having a color, thereby providing a positive indication that the vent cap 120 has been shifted to the second, actively depressed position. For example, in one embodiment, a transparent or translucent portion of housing 194 could have a blue hue, and the colored band 243 could be colored yellow, such that when the vent cap 120 is shifted to the second, actively depressed position the overlapping of colors appears green to a user, thereby visually indicating that vent cap has been fully shifted, and that any gaseous fluid trapped within the intravenous catheter assembly 100 has been vented.

In another embodiment, eyelet 214 can include a whistle 245, wherein the whistle 245 is configured to provide an audible indication that gaseous fluid within the intravenous catheter assembly 100 is being vented. When the audible indication ceases, a user will know that any gaseous fluid trapped within the intravenous catheter assembly 100 is being vented.

Figure 25:
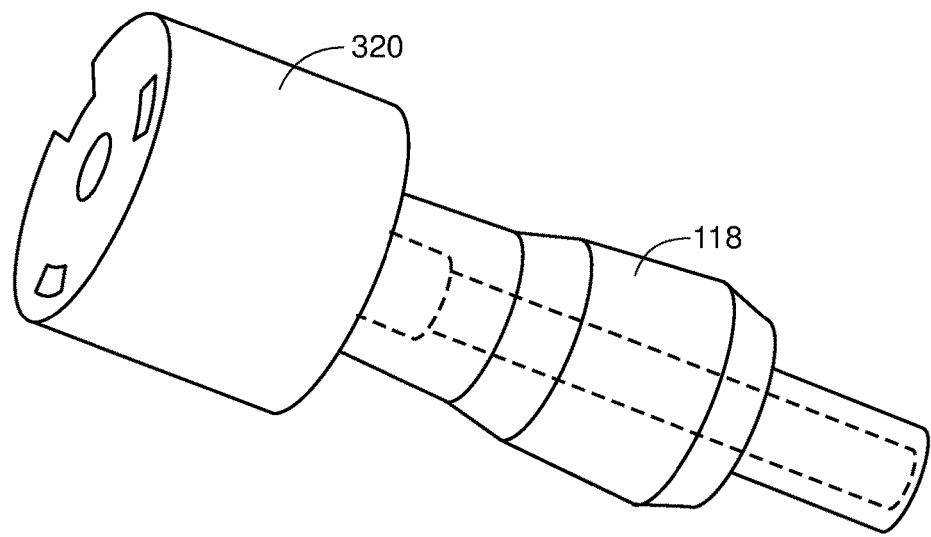
FIG. 25 is a perspective view depicting a self activating vent cap in accordance with an embodiment of the disclosure.
Figure 26A:
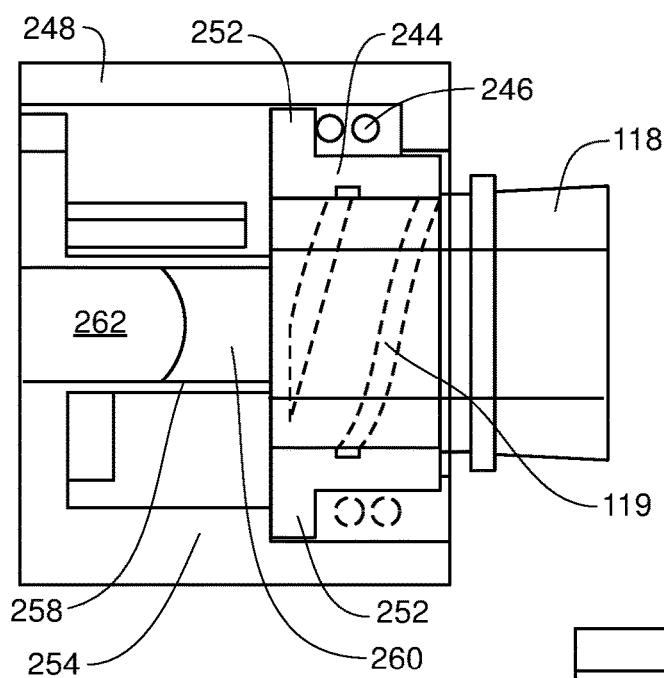
FIG. 26A is a cross sectional view of the vent cap of FIG. 25 coupled to a needleless connector in a first, storage position.
Figure 26B:
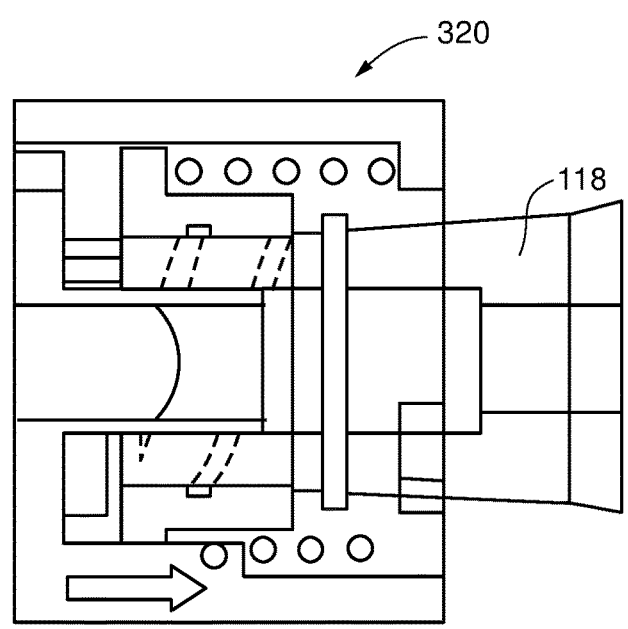
FIG. 26B is a cross sectional view of the vent cap of FIG. 26A coupled to the needleless connector in a second, activated position.

In another embodiment, the intravenous catheter assembly 100 can include a self activating vent cap 320. Referring to FIGS. 25-26B, a self activating vent cap 320 is depicted in accordance with an embodiment of the disclosure. In one embodiment, the self activating vent cap 320 can include a threaded portion 244, a biasing mechanism 246 such as a coil spring, and an activation portion 248. Self activating vent cap 320 can be shiftable between a first, storage position (as depicted in FIG. 26A) and a second, activated position (as depicted in FIG. 26B).

Threaded portion 244 can be operably coupleable to the needleless connector 118. For example, in one embodiment, threaded portion 244 is threadably coupled to the Luer lock connector 119 of the needleless connector 118. Threaded portion 244 can remain fixed in position relative to the needleless connector 118 during use, and can be uncoupled from the needleless connector 118 after use.

Activation portion 248 can at least partially surround the threaded portion 244 and can be distally shiftable relative to the threaded portion 244 and needleless connector 118 between the first, storage position and the second, activated position. Coil spring 246 can be positioned between the threaded portion 244 and the activation portion 248 to bias the activation portion to the second, activated position. In one embodiment, the coil spring 246 is positioned between a plurality of bosses of the activation portion 248 and one or more ridges 252 of the threaded portion 244. In one embodiment, distal shifting of the activation portion 248 relative to the threaded portion 244 can be precluded by the interference of least one ridge 252 of the threaded portion 244 with a ledge 254. Activation portion 248 can rotate relative to threaded portion 244 to eliminate the interference between the at least one ridge 252 and the ledge 254, thereby enabling the activation portion 248 to shift distally to the second, activated position.

Activation portion 248 can include a vent path wall 258 defining a vent path 260 plugged at a proximal end by a flash plug 262. Vent path wall 258 can be configured such that in the first, storage position, the distal end of the vent path wall 258 leaves the compression seal 192 (as depicted in FIG. 7A-C) of the needleless connector 118 in an uncompressed state, and in the second activated position, the vent path wall 258 extends into the needleless connector 118 to compress the compression seal 192, thereby enabling the gas trapped within the intravenous catheter assembly 100 to vent through the air permeable flash plug 262.

In one embodiment, the self activating vent cap 320 can be shipped in the first storage position with the threaded portion 244 threadably coupled to the needleless connector 118, thereby guarding against the permanent deformation of the compression seal 192 when subjected to compression over time. Prior to connection of the needleless connector 118 to an IV fluid supply connector 186, the self activating vent cap 320 can be removed from the needleless connector 118. To remove the self activating vent cap 320, a clinician can grip the activation portion 248 and rotate the activation portion 248 relative to the needleless connector 118, causing the activation portion 248 to rotate relative to the threaded portion 244, thereby causing the self activating vent cap 320 to shift to the second, actively depressed position. Further rotation of the activation portion 248 causes the threaded portion 244 to become uncoupled from the needleless connector 118.

Figure 27A:
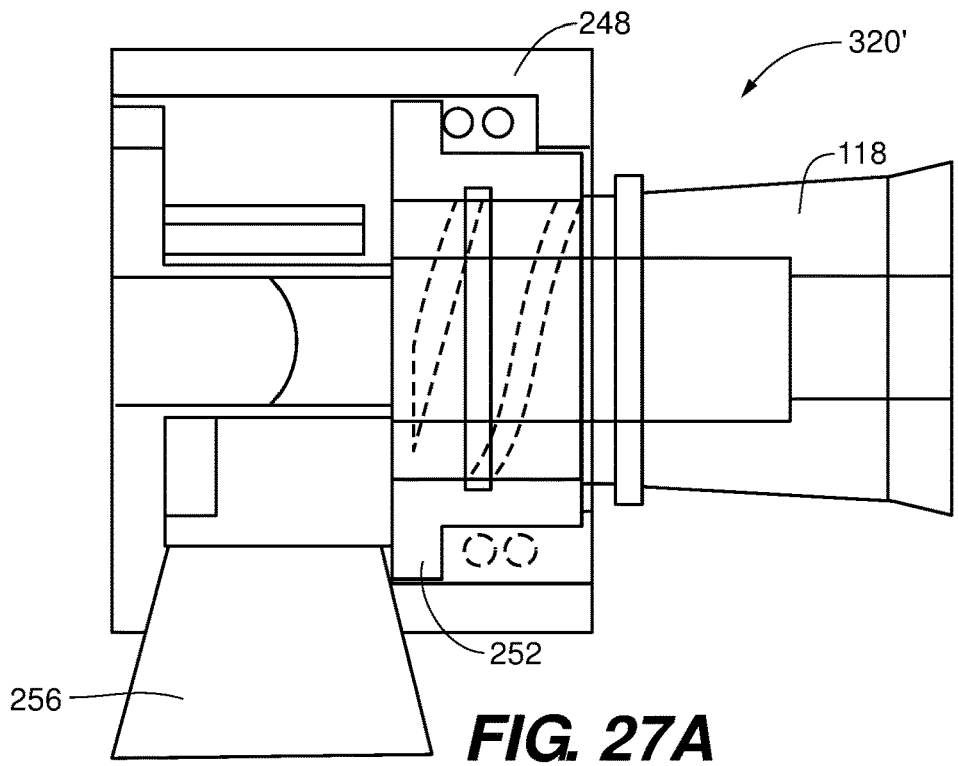
FIG. 27A is a cross sectional view depicting a self activating vent cap coupled to a needleless connector in a first, storage position in accordance with a second embodiment of the disclosure.
Figure 27B:
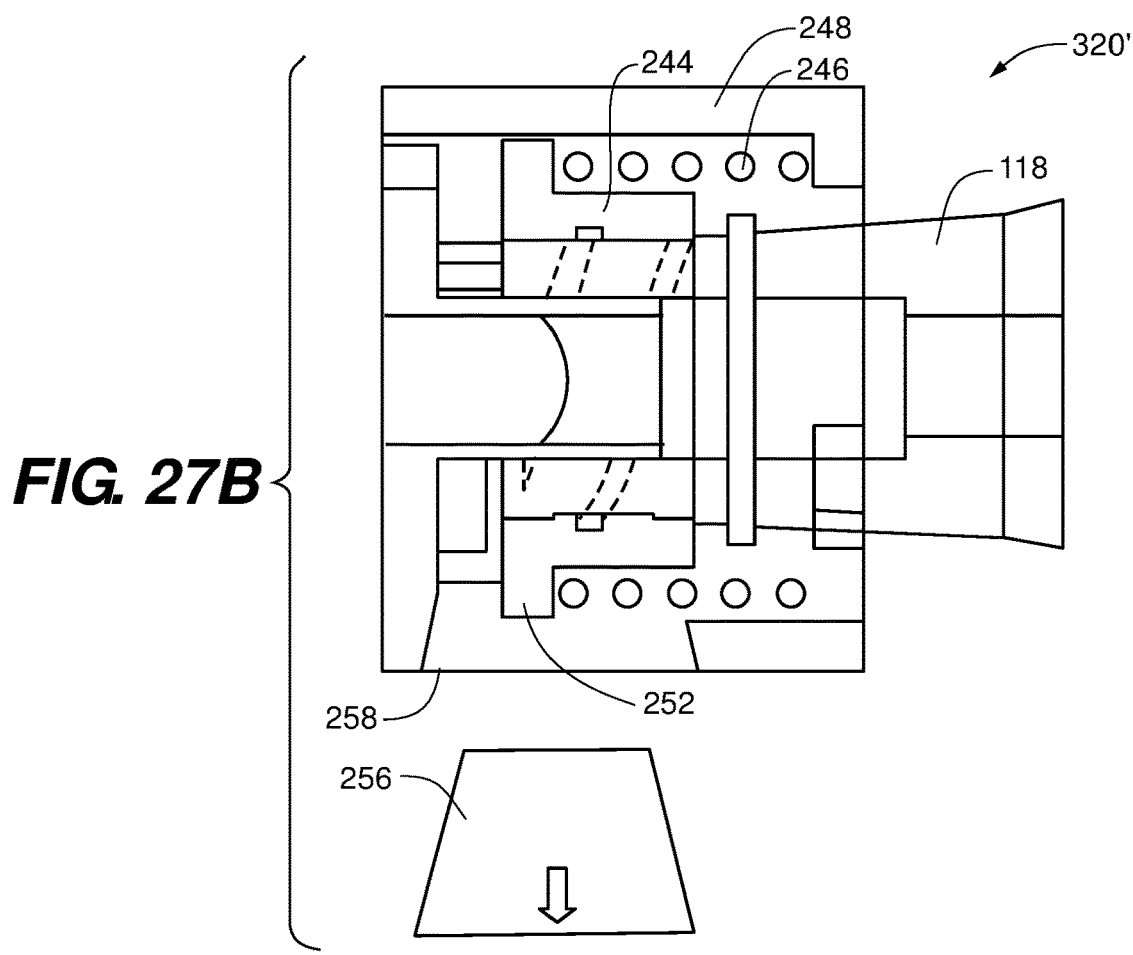
FIG. 27B is a cross sectional view depicting the self activating vent cap of FIG. 27A coupled to a needleless connector in a second, activated position.

Referring to FIGS. 27A-B, another embodiment of a self activating vent cap 320' is depicted in accordance with the disclosure. In this embodiment, the ledge 254 can be replaced with a blocking member 256. Blocking member 256 can be selectively inserted and removed from an aperture 258 defined by the activation portion 248. In one embodiment, distal shifting of the activation portion 248 relative to the threaded portion 244 can be precluded by the interference of least one ridge 252 of the threaded portion 244 with the blocking member 256, thereby retaining the self activating vent cap 320' in a first, storage position (as depicted in FIG. 27A). Upon removal of the blocking member 256, the coil spring 246 can cause the activation portion 248 to shift relative to the threaded portion 244, thereby shifting the self activating vent cap 320' to the second, activated position (as depicted in FIG. 27B). For example, in one embodiment, the blocking member 256 is operably coupled to packaging of the intravenous catheter assembly 100.

In one embodiment, the self activating vent cap 320' can be shipped in the first storage position with the threaded portion 244 threadably coupled to the needleless connector 118, thereby guarding against the permanent deformation of the compression seal 192 when subjected to compression over time. Prior to connection of the needleless connector 118 to an IV fluid supply connector 186, the self activating vent cap 320' can be removed from the needleless connector 118. Prior to removal of the self activating vent cap 320', a clinician can be required to remove the blocking member 256, thereby, causing the self activating vent cap 320' to shift to the second, actively depressed position. Rotation of the self activating vent cap 320' relative to the needleless connector 118 can cause the threaded portion 244 to become uncoupled from the needleless connector 118.

Figure 28A:
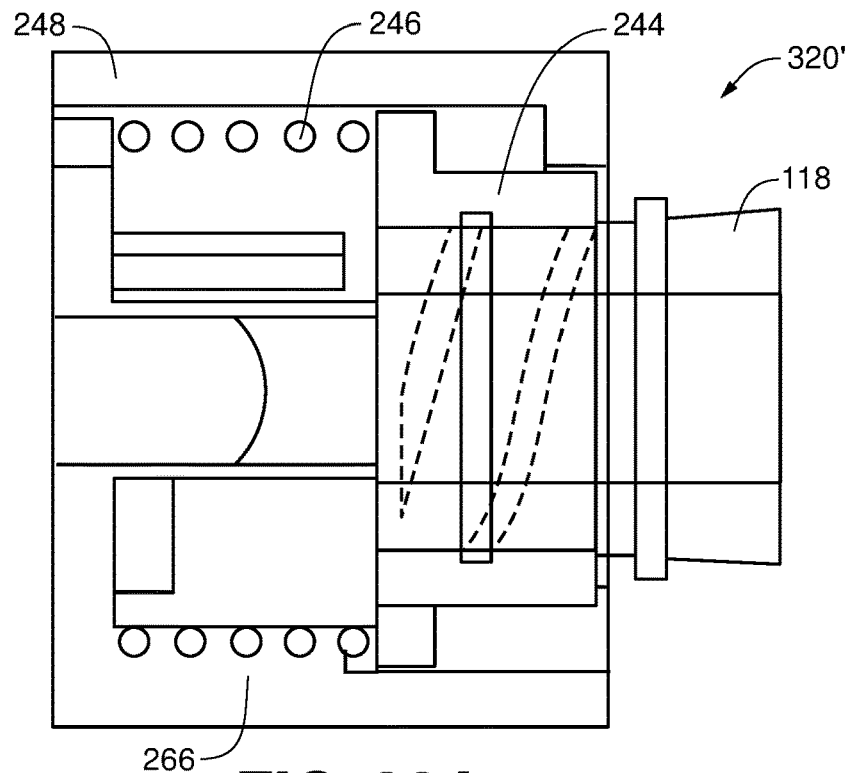
FIG. 28A is a cross sectional view depicting a vent cap coupled to a needleless connector in a first, storage position in accordance with a second embodiment of the disclosure.
Figure 28B:
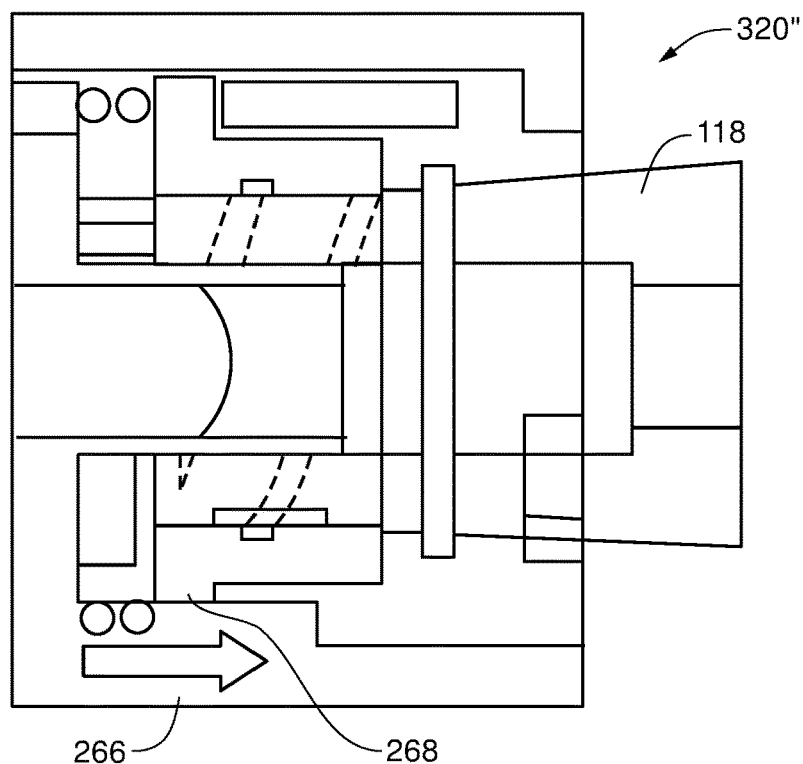
FIG. 28B is a cross sectional view depicting the vent cap of FIG. 28A coupled to a needleless connector in a second, activated position.

Referring to FIGS. 28A-B, another embodiment of a vent cap 320" is depicted in accordance with the disclosure. In this embodiment, the coil spring 246 can be configured to bias the vent cap 320" to the first, storage position (as depicted in FIG. 28A). To remove the vent cap 320" from the needleless connector 118, a clinician can depress the activation portion 248 to the second, activated position (as depicted in FIG. 28B) in order to engage a keyed portion 266 of the activation portion 248 with a corresponding groove 268 of the threaded portion 244, so that the threaded portion 244 couples with the activation portion 248, such that rotation of the activation portion 248 causes rotation of the threaded portion, thereby enabling the threaded portion to be uncoupled from the needleless connector 118. Conversely, without depressing the activation portion 248 to the second, activated position, the activation portion 248 can rotate freely such that it does not engage the threaded portion 248. Like previous embodiments, when the activation portion 248 is shifted to the second, activated position, gas trapped within the intravenous catheter assembly 100 can be vented. Accordingly, by requiring a clinician to shift the vent cap 320" to the second, activated position prior to unthreading the vent cap 320" from the needleless connector, the likelihood of an inadvertent or premature removal of the vent cap 320" from the needleless connector 118 before proper venting of gas trapped therein can be reduced.

Figures 29A, 29B:
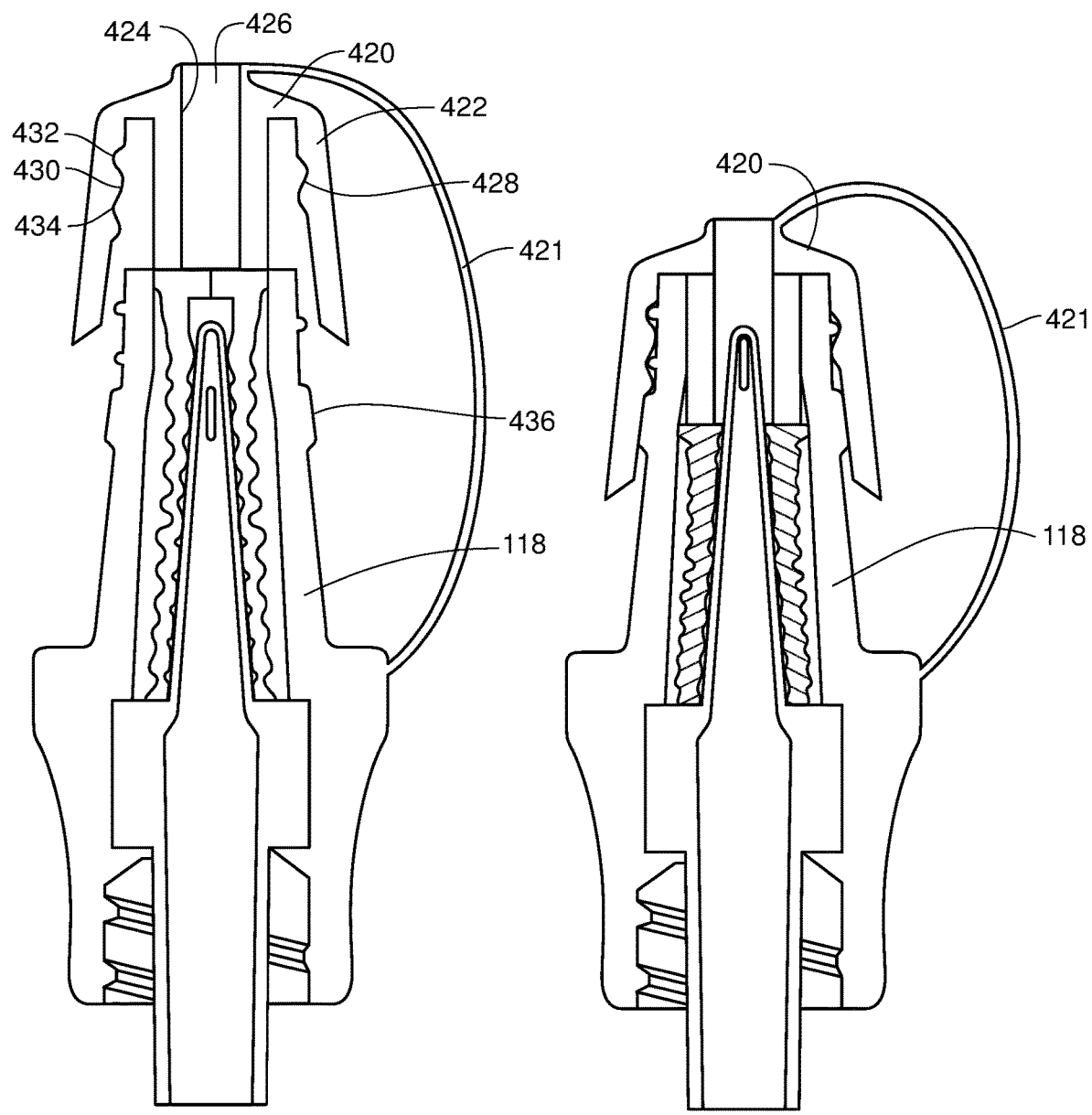
FIG. 29A is a cross sectional view depicting a vent cap coupled to a needleless connector in an initial, storage position in accordance with an embodiment of the disclosure, wherein the vent cap includes a threaded portion configured to emit an audible clicking sound when rotated.
FIG. 29B is a cross-sectional view of the vent cap and needleless connector of FIG. 29A, wherein the vent cap is in a second, actively depressed position.

Referring to FIGS. 29A-B, a threaded vent cap 420 is depicted in accordance with an embodiment of the disclosure. In one embodiment, the vent cap 420 can be threadably engaged with needleless connector 118 in a first, storage position (as depicted in FIG. 29A). Rotation of the vent cap 420 relative to the needleless connector 118 can cause the vent cap 420 to shift relative to the needleless connector 118 to a second, activated position (as depicted in FIG. 29B). Further, in one embodiment, the vent cap 420 can be tethered to the needleless connector 118 via a leash 421, thereby precluding the vent cap 420 from inadvertently being lost or misplaced. In other embodiments, the vent cap 420 can be tethered to other portions of the intravenous catheter assembly 100.

In one embodiment, threaded vent cap 420 can include a threaded vent cap body 422 defining a vent path/air permeable barrier socket 424, configured to receive an air permeable barrier 426. An interior wall 428 can include a plurality of threads 430 for engagement with the needleless connector 118. In one embodiment, the geometric profile of the thread 430 can be symmetrical, such that the top 432 and the bottom 434 of the thread 430 have the same angle. In another embodiment, the profile of the thread 430 can be asymmetrical, such that either of the top 432 or the bottom 434 has a shallower angle than that of the respective bottom 434 or top 432. Such asymmetry can guard against over threading the threaded vent cap 420 as well as providing an audible clicking sound to a user, as the threads 430 jump over the respective threads of the needleless connector 118 as a user continues to tighten the threaded vent cap 420 after reaching the second, activated position. In one embodiment, the needleless connector 118 can include a circumferential ridge 436, configured to aid in inhibiting further distal movement of the vent cap body 422 upon reaching the second, activated position.

Figure 30A:
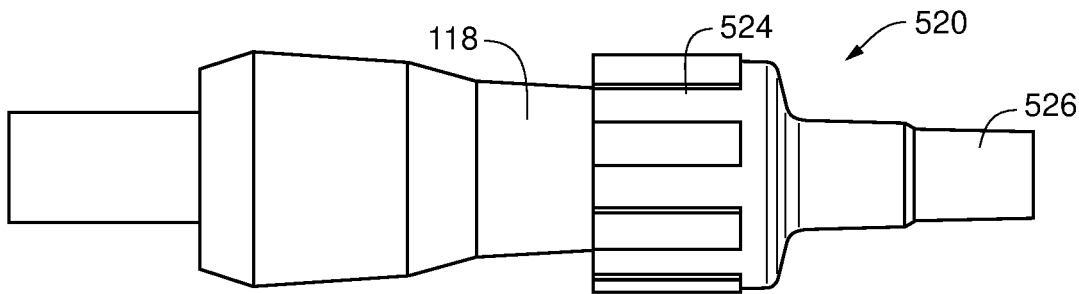
FIG. 30A is a profile view depicting a reversible vent cap coupled to a needleless connector in a first storage position in accordance with an embodiment of the disclosure.
Figure 30B:
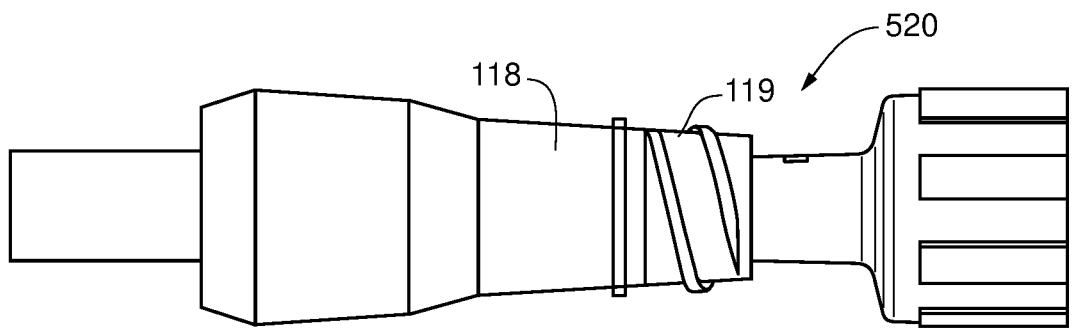
FIG. 30B is a profile view depicting the reversible vent cap of FIG. 30B coupled to a needleless connector in a second, actively depressed position.
Figure 31:
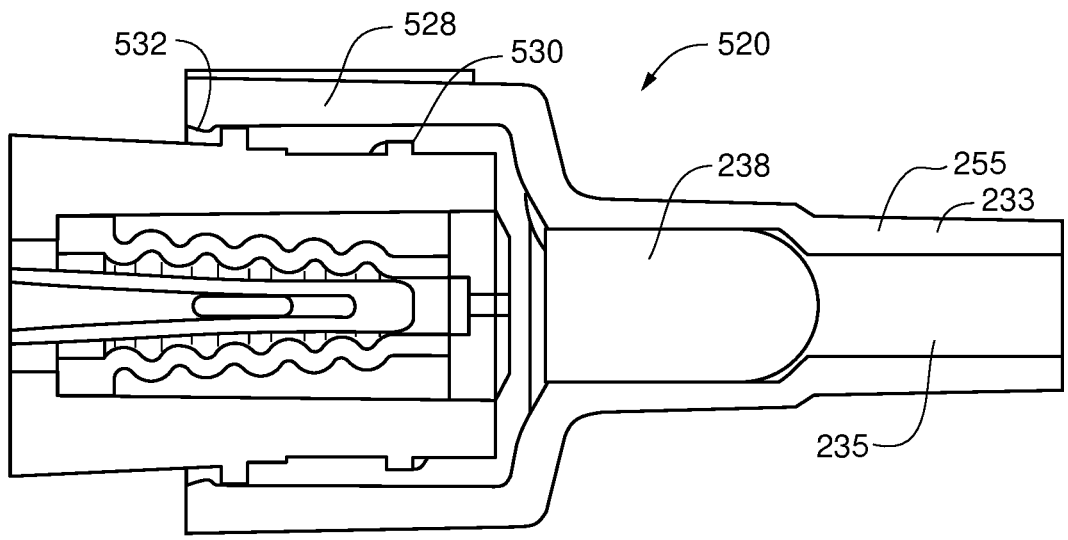
FIG. 31 is a cross sectional view depicting the reversible vent cap of FIG. 30A coupled to a needleless connector in the first, storage position.

Referring to FIGS. 30A-31, another embodiment of a threaded vent cap 520 is depicted in accordance with the disclosure. Vent cap 520 can include a connection end 524 and an activation end 526. In a storage position (as depicted in FIGS. 30A and 31) the connection end 524 can be configured to operably couple to the needleless connector 118. For example, in one embodiment, the connection end 524 can include a cup portion 528 having an internal wall 530 defining an internal thread 532 configured to threadably coupled to a Luer lock 119 of the needleless connector 118.

In one embodiment, the activation end 255 can include a vent path wall 233 defining a vent path 235 housing a flash plug 238. When venting of the intravenous catheter assembly 100 is desired, the connection end can be uncoupled from the needleless connector 118, and the activation end 526 can be inserted into the needleless connector 118, such that the vent path wall 235 extends into the needleless connector 118 to compress the compression seal 192, thereby enabling the gas trapped within the intravenous catheter assembly 100 to vent through the air permeable flash plug 238.

Figure 32:
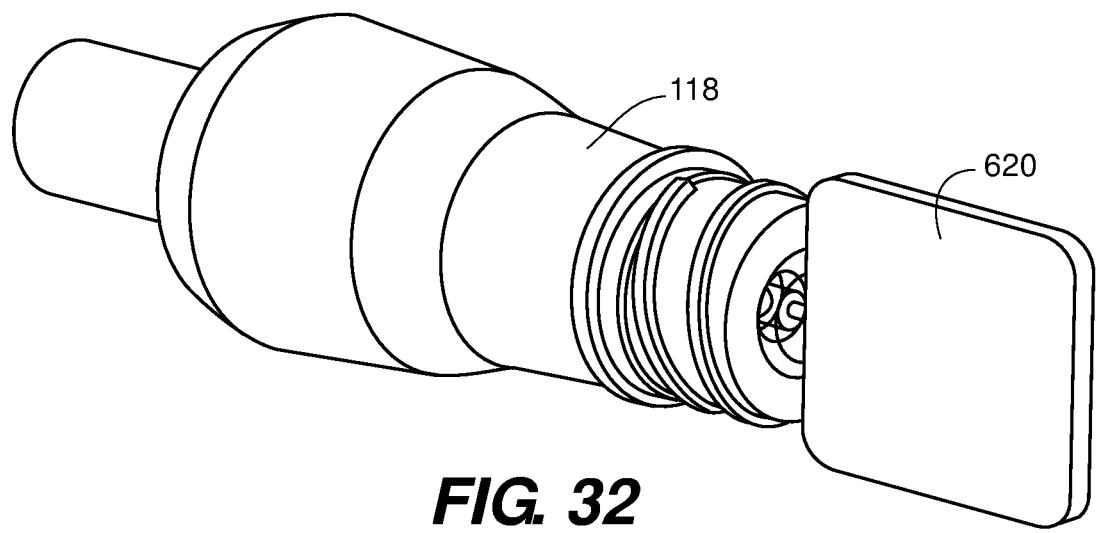
FIG. 32 is a perspective view depicting a mandrel inserted into the compression seal of a needleless connector in accordance with an embodiment of the disclosure.
Figure 33:
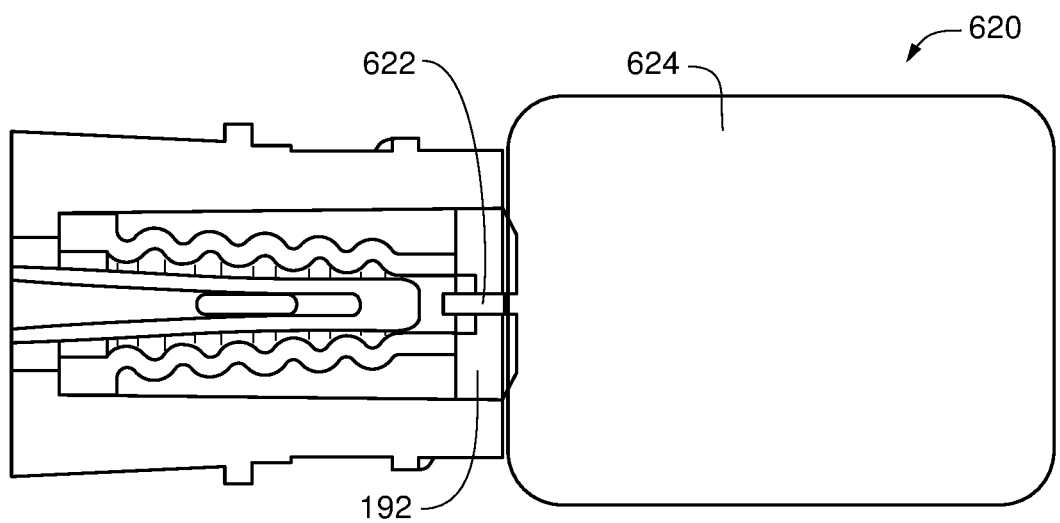
FIG. 33 is a cross sectional view depicting the mandrel of FIG. 32 inserted into the compression seal of a needleless connector.
Figure 34:
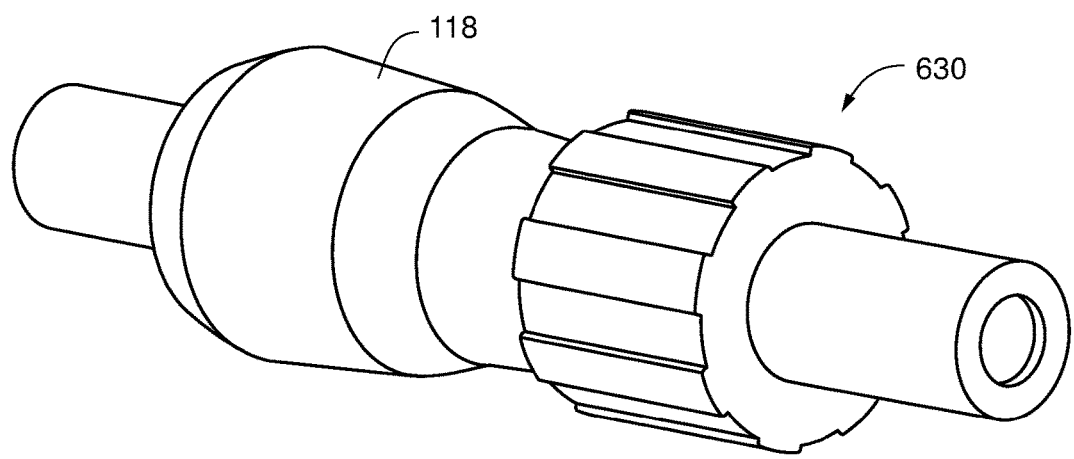
FIG. 34 is a perspective view depicting a vent cap having a mandrel coupled to a needleless connector in accordance with an embodiment of the disclosure.
Figure 35:
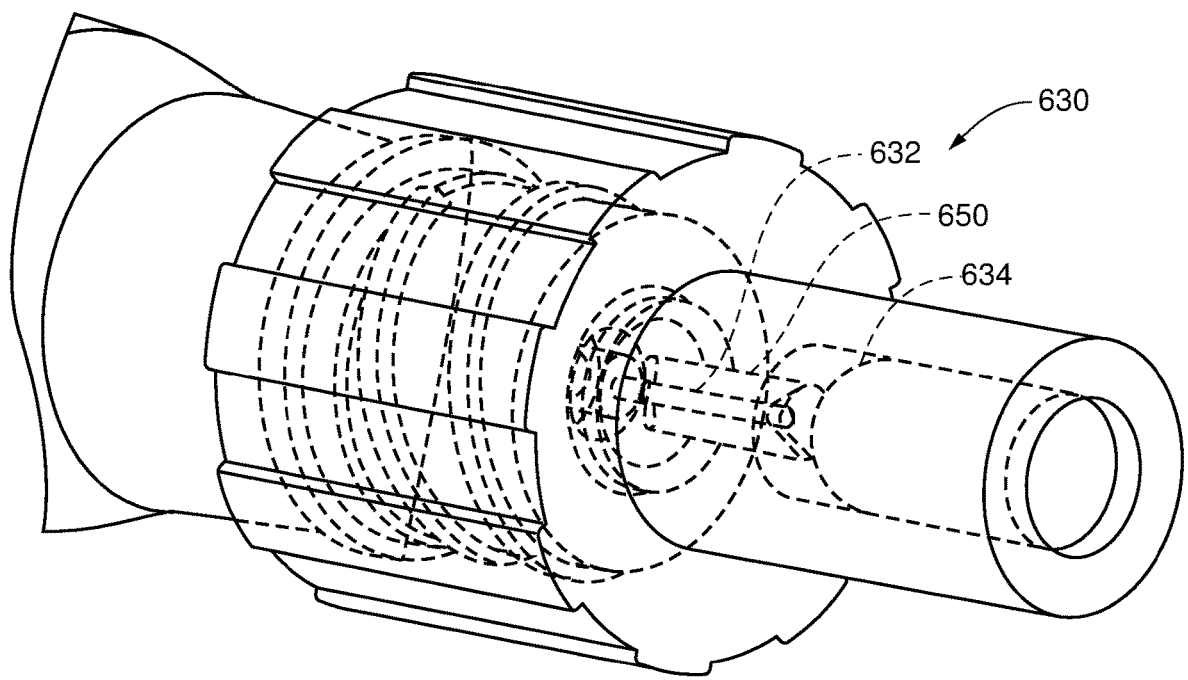
FIG. 35 is a perspective view depicting the vent cap of FIG. 34 showing hidden lines.
Figure 36:
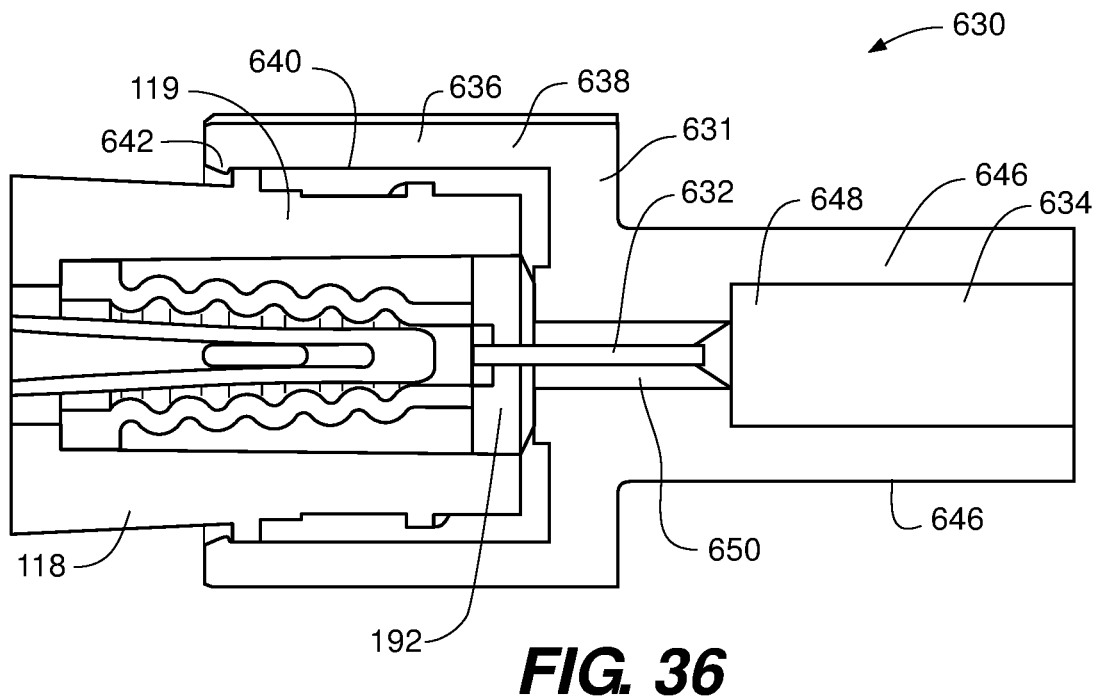
FIG. 36 is a cross sectional view depicting the vent cap of FIG. 34 coupled to a needleless connector in accordance with an embodiment of the disclosure.
Figure 37:
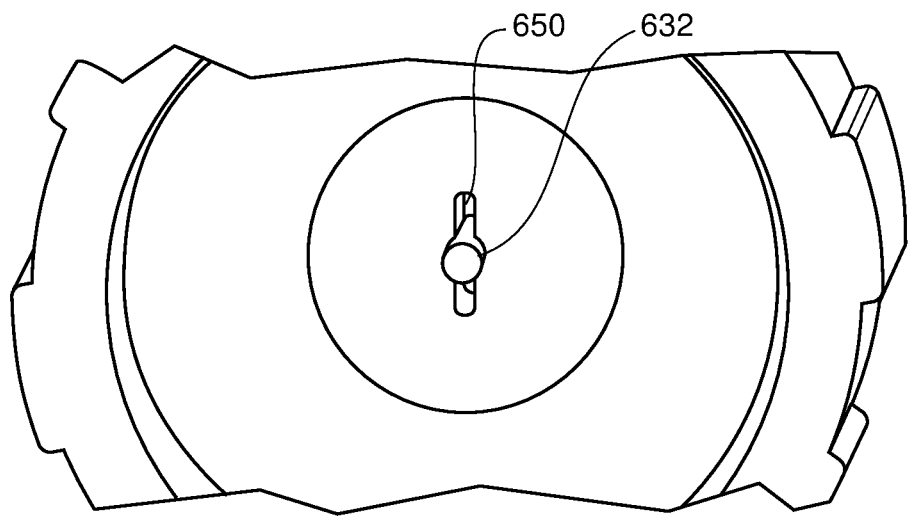
FIG. 37 is a close-up partial perspective view of the vent cap of FIG. 34 in accordance with an embodiment of the disclosure.

Referring to FIGS. 32 and 33, another embodiment of a vent cap 620 is depicted in accordance with the disclosure. In this embodiment, the vent cap 620 can include a mandrel 622 and a handle or gripping portion 624. In some embodiments, the vent cap 620 can be constructed of plastic. The mandrel 622 can be configured as a narrow rod insertable through a portion of the compression seal 192, thereby breaking the seal so as to enable air or gas trapped within the intravenous catheter assembly 100 to escape, while generally inhibiting the passage of fluid.

Referring to FIGS. 34-37, another embodiment of a vent cap 630 is depicted in accordance with the disclosure. Like the previous embodiment, the vent cap 630 can include a mandrel 632 configured to be inserted through a portion of the compression seal 192, thereby breaking the seal so as to enable air or gas trapped within the intravenous catheter assembly 100 to escape, while inhibiting the passage of fluid. To further aid in inhibiting the passage of fluid, air or gas escaping from the intravenous catheter assembly 100 can pass through a flash plug 634.

In one embodiment, the vent cap 630 can include a vent cap body 631 having a connection portion 636 and a vent portion. The connection portion 636 can be configured to operably couple to the needleless connector 118. For example, in one embodiment, the connection end 636 can include a cup shaped receptacle 638 having an internal surface 640 defining an internal thread 642 configured to, for example, threadably couple to a Luer lock 119 of the needleless connector 118.

The vent portion can include a vent path wall 646 defining a vent path 648 housing a flash plug 634. In one embodiment, a portion 650 of the vent path 648 can at least partially surround the mandrel 632, so as to enable air or gas to escape from the intravenous catheter assembly 100 with minimal resistance. In one embodiment, the portion 650 of the vent path 648 at least partially surrounding the mandrel 632 can be configured as a slot in which the mandrel 632 is positioned.

Accordingly, in one embodiment, as the vent cap 630 is threaded onto the needleless connector 118, the mandrel 632 passes through a small slit defined in the compression seal 192, thereby enabling air or gas trapped within the intravenous catheter assembly 100 to escape through the slit provided by the mandrel 632 under the pressure of bodily fluid. Thereafter, the escaping gas can pass through portion 650 of the vent path 648 and through the gas permeable flash plug 634 and into the atmosphere.

Figure 38:
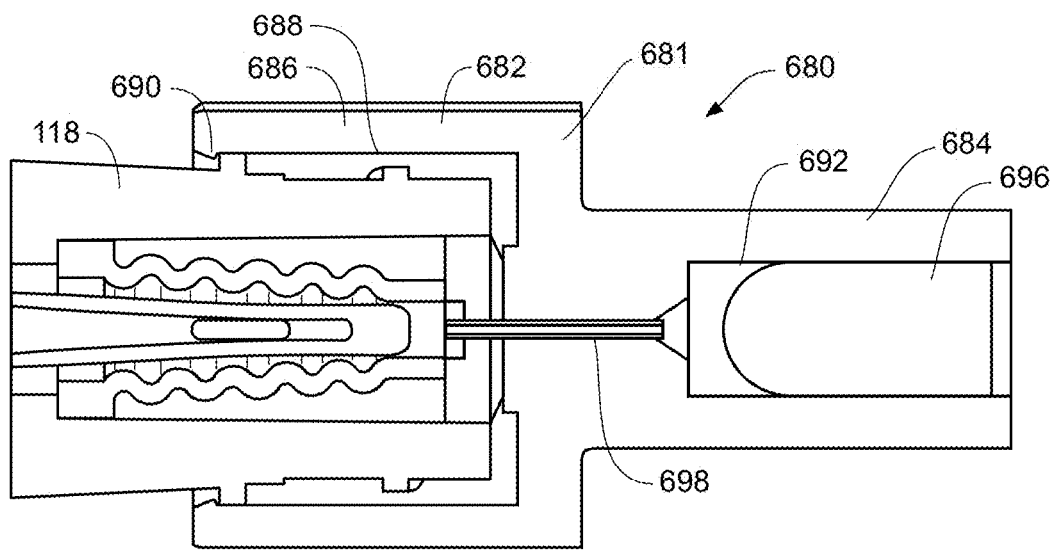
FIG. 38 is a cross sectional view depicting a vent cap with a cannula inserted into a compression seal of a needleless connector in accordance with an embodiment of the disclosure.
Figure 39:
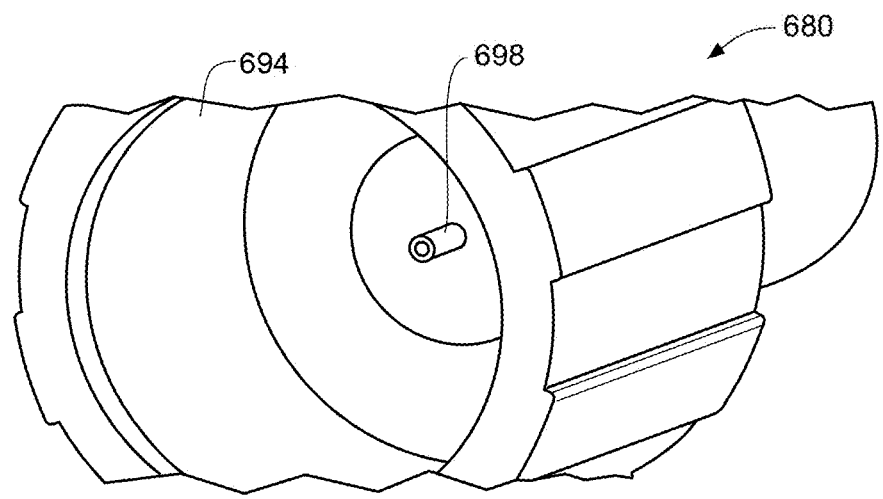
FIG. 39 is a close-up, partial perspective view of the vent cap of FIG. 38.

Referring to FIGS. 38-39, another embodiment of a vent cap 680 is depicted in accordance with the disclosure. Vent cap 680 can include a vent cap body 681 having a connection portion 682 and a vent portion 684. The connection portion 682 can be configured to operably couple to the needleless connector 118. For example, in one embodiment, the connection portion 682 can include a cup shaped receptacle 686 having an internal surface 688 defining an internal thread 690 configured to, for example, threadably couple to a Luer lock 119 of the needleless connector 118.

The vent portion 684 can include a vent path wall 692 defining a vent path 694 housing a flash plug 696. A cannula 698 operably coupled between the connection portion 682 and the vent portion 684 can create a fluid path between the cup portion 686 and the vent path 694, thereby enabling air or gas to flow from the interior of the cup portion 686 into the vent path 694.

Accordingly, in one embodiment, as the vent cap 680 is threaded onto the needleless connector 118, the cannula 698 passes through a small slit defined in the compression seal 192, thereby enabling air or gas trapped within the intravenous catheter assembly 100 to escape through the fluid path provided by the cannula 698 under the pressure of bodily fluid. Thereafter, the escaping gas can pass through the vent path 648, the gas permeable flash plug 634, and into the atmosphere.

Various example embodiments catheters are described herein for use in accessing the vein of the patient or subject. It is to be appreciated, however, that the example embodiments described herein can alternatively be used to access the vasculature of the subject at locations other than the vein, including but not limited to the artery of the subject. It is additionally to be appreciated that the term "clinician" refers to any individual that can perform the catheter insertion procedure with any of the example embodiments described herein or alternative combinations thereof. Similarly, the term "patient" or "subject" as used herein, is understood to refer to an individual or an object in which the catheter is to be inserted, whether human, animal, or inanimate. Various descriptions are made herein, for the sake of convenience, with respect to the procedures being performed by the clinicians to access the vein of the subject, while the disclosure is not limited in this respect.

It is also to be appreciated that the term "distal," as used herein, refers to the direction along the axis of the insertion substantially parallel to the central axis of the insertion needle that is closest to the subject during catheter insertion. Conversely, the term "proximal," as used herein, refers to the direction along the axis of insertion substantially parallel to the central axis of the insertion needle that is further away from the subject during catheter insertion.

III. Operation

In operation, placement of the intravenous catheter assembly 100 generally includes the preparation of the biological site of the patient. Often a tourniquet is applied proximal to the biological site and a variety of techniques can be used to dilate the patient's vein. While wearing disposable gloves, the clinician cleanses the biological site and a vein is retracted or anchored by placing a thumb over the vein about 50 to 75 mm away from the site.

To prepare the intravenous catheter assembly 100 for use, the clinician removes the sheath 22 to expose the insertion needle. The clinician also depresses the vent cap 120, or causes the vent cap 120 to be activated or depressed from the initial storage position, where the vent cap 120 is assembled to the needleless connector without compression the seal 192 of the needleless connector 118, to a second activated position where the vent cap 120 compresses the seal 192 and opens the needle free connector 118. In the second activated positon, gas or air but not bodily fluid (e.g., blood) may be purged from the catheter assembly during venipuncture.

The needle 104 and the catheter tube 108 are introduced into the vein by inserting the bevel of the sharpened needle tip 106 into the vein at about a 20-30° angle, with the bevel facing up in order to pierce one wall of the vein. In some embodiments, during this process, the clinician grips the catheter insertion device 102 for optimum control. If successful, blood from the vein flows through the lumen of the needle 104 and into a flashback chamber, thereby providing primary flashback. Secondary flashback can also occur as blood enters the extension tubing as air is purged therefrom.

To finish placement, the intravenous catheter assembly 100 is lowered towards the skin to decrease the entry angle, and the catheter tube 108 is advanced slightly into the vein. The needle 104 is loosened and the catheter tube 108 is gently advanced further into the vein until the catheter hub 110 is against the biological site. The tourniquet can then be loosened and the needle 104 can be withdrawn from the catheter tube 108. As the needle is withdrawn, the sharpened needle tip 106 is withdrawn through the catheter lumen 128 and the septum 132. As the sharpened needle tip 106 passes through the septum 132, the self-sealing nature of the septum 132 closes any void left by the needle 104 to create a fluid tight barrier.

With air purged from the extension tube 114 and needleless connector 118, the vent cap 120 may be removed from the needleless connector 118 and discarded. The needleless connector 118 moves from the open position to the closed position as the vent cap 120 is removed therefrom. In this respect, the escape of bodily fluid from the catheter assembly 100 is inhibited.

The clinician can then secure the catheter tube 108 in place by securing the catheter hub 110 and/or wings 112 to the biological site by gauze and adhesive tape. According to an alternate approach, the air or gaseous fluid trapped within the intravenous catheter assembly 100 can be vented by moving the vent cap 120 from the first, storage position to the second actively depressed position after venipuncture, thereby both evacuating the air within the intravenous catheter assembly 100 and providing an indication of secondary flashback to confirm placement of the catheter tube 108 in the patient's vein.

Needleless connector 118 can then be connected to an IV fluid supply connector 186 configured to supply medicament to a patient, or withdraw fluid from the patient. Extension tube clamp 116 can be manipulated as desired to open and close the fluid path of the extension tube 114.

It should be understood that the individual steps used in the methods of the present teachings may be performed in any order and/or simultaneously, as long as the teaching remains operable. Furthermore, it should be understood that the apparatus and methods of the present teachings can include any number, or all, of the described embodiments, as long as the teaching remains operable.

Persons of ordinary skill in the relevant arts will recognize that embodiments may comprise fewer features than illustrated in any individual embodiment described above. The embodiments described herein are not meant to be an exhaustive presentation of the ways in which the various features may be combined. Accordingly, the embodiments are not mutually exclusive combinations of features; rather, embodiments can comprise a combination of different individual features selected from different individual embodiments, as understood by persons of ordinary skill in the art. Moreover, elements described with respect to one embodiment can be implemented in other embodiments even when not described in such embodiments unless otherwise noted. Although a dependent claim may refer in the claims to a specific combination with one or more other claims, other embodiments can also include a combination of the dependent claim with the subject matter of each other dependent claim or a combination of one or more features with other dependent or independent claims. Such combinations are proposed herein unless it is stated that a specific combination is not intended. Furthermore, it is intended also to include features of a claim in any other independent claim even if this claim is not directly made dependent to the independent claim.

Moreover, reference in the specification to "one embodiment," "an embodiment," or "some embodiments" means that a particular feature, structure, or characteristic, described in connection with the embodiment, is included in at least one embodiment of the teaching. The appearances of the phrase "in one embodiment" in various places in the specification are not necessarily all referring to the same embodiment.

Any incorporation by reference of documents above is limited such that no subject matter is incorporated that is contrary to the explicit disclosure herein. Any incorporation by reference of documents above is further limited such that no claims included in the documents are incorporated by reference herein. Any incorporation by reference of documents above is yet further limited such that any definitions provided in the documents are not incorporated by reference herein unless expressly included herein.

For purposes of interpreting the claims, it is expressly intended that the provisions of Section 112, sixth paragraph of 35 U.S.C. are not to be invoked unless the specific terms "means for" or "step for" are recited in a claim.

What is claimed is:

1. A vent cap configured to be coupled to a needleless connector and shiftable relative to the needleless connector between a storage position and an actively depressed, venting position, the vent cap comprising:
    a threaded portion configured to be selectively threadably coupled to the needleless connector, such that the threaded portion is coupled to the needleless connector during use, and is uncoupled from the needleless connector after use;
    an activation portion at least partially surrounding the threaded portion and shiftable relative to the threaded portion between the storage position, in which the needleless connector remains sealed, and the actively depressed, venting position, in which a wall defining a vent path is at least partially inserted into the needleless connector, thereby enabling gas within the needleless connector to vent therefrom; and
    wherein the vent cap is configured such that actively depressing the activation portion distally to the actively depressed, venting position enables the threaded portion to couple with the activation portion, whereupon rotation of the activation portion causes rotation of the threaded portion to threadably uncouple the vent cap from the needleless connector.

2. The vent cap of claim 1, further comprising a biasing mechanism positioned between the threaded portion and the activation portion and configured to bias the activation portion to the storage position.

3. The vent cap of claim 1, wherein the threaded portion is configured to be selectively threadably coupled to a Luer lock connector of the needleless connector.

4. The vent cap of claim 3, wherein depressing the activation portion distally relative to the threaded portion and rotating the activation portion causes the threaded portion to become threadably uncoupled from the Luer lock connector.

* * * * *

UNITED STATES PATENT AND TRADEMARK OFFICE
CERTIFICATE OF CORRECTION

| | |
|---|---|
| PATENT NO. | : 11,202,897 B2 |
| APPLICATION NO. | : 16/315044 |
| DATED | : December 21, 2021 |
| INVENTOR(S) | : Abitabilo et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 192 days.

Signed and Sealed this
Tenth Day of September, 2024

Katherine Kelly Vidal
*Director of the United States Patent and Trademark Office*